US009278137B2

(12) United States Patent
Amgoune et al.

(10) Patent No.: US 9,278,137 B2
(45) Date of Patent: Mar. 8, 2016

(54) POLYMERIC CONJUGATES OF ACTIVE PRINCIPLES, THEIR PROCESS OF PREPARATION AND THEIR POLYMERIC INTERMEDIATES

(75) Inventors: Abderrhamane Amgoune, Toulouse (FR); Didier Bazile, Paris (FR); Fethi Bensaid, Toulouse (FR); Didier Bourissou, Plaisance du Touch (FR); Eric Didier, Paris (FR); Stephanie Greco, Paris (FR); Harivardhan Reddy Lakkireddy, Paris (FR); Serge Sable, Paris (FR); Michel Veillard, Paris (FR)

(73) Assignees: SANOFI, Paris (FR); CENTRE NATIONAL DE LA RECHERCHE SCIENTIFIQUE (C.N.R.S.), Paris (FR); UNIVERSITE PAUL SABATIER TOULOUSE III, Toulouse (FR)

( * ) Notice: Subject to any disclaimer, the term of this patent is extended or adjusted under 35 U.S.C. 154(b) by 71 days.

(21) Appl. No.: 13/877,757

(22) PCT Filed: Nov. 18, 2011

(86) PCT No.: PCT/EP2011/070441
§ 371 (c)(1),
(2), (4) Date: Apr. 4, 2013

(87) PCT Pub. No.: WO2012/066117
PCT Pub. Date: May 24, 2012

(65) Prior Publication Data
US 2013/0243719 A1    Sep. 19, 2013

(30) Foreign Application Priority Data
Nov. 19, 2010 (FR) ..................... 10 59561

(51) Int. Cl.
*A61K 47/48* (2006.01)
*C08G 65/332* (2006.01)

(52) U.S. Cl.
CPC ......... *A61K 47/48215* (2013.01); *A61K 47/488* (2013.01); *A61K 47/48192* (2013.01); *A61K 47/48907* (2013.01); *C08G 65/3328* (2013.01)

(58) Field of Classification Search
CPC ................. A61K 47/48192; A61K 47/48215; A61K 47/488; A61K 47/48907; C08G 65/3328
USPC ........................ 424/78.3; 525/437; 528/272
See application file for complete search history.

(56) References Cited

U.S. PATENT DOCUMENTS

| 5,766,635 A | 6/1998 | Spenleuhauer et al. |
| 2011/0237686 A1* | 9/2011 | Ng et al. .............. 514/772.1 |

FOREIGN PATENT DOCUMENTS

| WO | WO-99/17804 A1 | 4/1999 |
| WO | WO 2007/110003 A2 | 10/2007 |

OTHER PUBLICATIONS

Nederberg et al. (Biomacromolecules 2009, vol. 10, 1460-1468).*
Nederberg et al. (Biomacromolecules 2009, 10 1460-1468).*
Zhang et al. (Biomaterials 26 (2005) 2121-2128).*
Nederberg et al., "Simple Approach to Stabilized Micelles Employing Miktoarm Terpolymers and Stereocomplexes with Application in Paclitaxel Delivery", Biomacromolecules (2009), vol. 10, No. 6, pp. 1460-1468.
Yoo et al., "Doxorubicin-conjugated biodegradable polymeric micelles having acid-cleavable linkages", Journal of Controlled Release (2002), vol. 82, No. 1, pp. 17-27.
Zhang et al., "Synthesis and characterization of the paclitaxel/MPEG-PLA block copolymer conjugate", Biomaterials (2005), vol. 26, No. 14, pp. 2121-2128.
International Search Report dated Dec. 12, 2011 issued in PCT/EP2011/070441.
Gaucher, G. et al. (Apr. 2, 2010). "Polyester-Based Micelles and Nanoparticles for the Parenteral Delivery of Taxanes," *J. of Controlled Release* 143(1):2-12.
Tong, R. et al. (2008). "Paclitaxel-Initiated, Controlled Polymerization of Lactide for the Formulation of Polymeric Nanoparticulate Delivery Vehicles," *Angew. Chem. Int. Ed. Engl.* 47(26):4830-4834.

* cited by examiner

*Primary Examiner* — Anna Falkowitz
(74) *Attorney, Agent, or Firm* — Morrison & Foerster LLP

(57) ABSTRACT

The present invention relates to novel conjugates of active principles grafted to a polymer, to the nanoparticles comprising them, to their preparation and to their polymeric intermediates.

16 Claims, 2 Drawing Sheets

POLYMERIC CONJUGATES OF ACTIVE PRINCIPLES, THEIR PROCESS OF PREPARATION AND THEIR POLYMERIC INTERMEDIATES

The present invention relates to polymeric conjugates of active principles, in particular of taxoids.

Taxoids have generally in common a very low solubility in water. Thus, the taxol is formulated in a mixture of cremophor and alcohol which causes significant side effects, such as hypersensitivity, nephrotoxicity, cardiotoxicity and neurotoxicity. Alternative formulations have been sought for; in particular, water-soluble formulations based on polymers, such as microspheres, nanoparticles and micelles, have been explored with the objective of providing alternative and effective administration forms (Gaucher et al., *J. of Controlled Release*, 143 (2010), 2-12).

Particles of nanometric size are particularly advantageous in that their small size would allow them to reach tumour tissues and their structure, comprising a hydrophilic corona, would make it possible to prolong the systemic circulation time.

Thus, U.S. Pat. No. 5,766,635 describes nanoparticles of active principles prepared from copolymers of polyethylene glycol and of polylactic acid, the nanoparticles being formed by simple precipitation. Nevertheless, the nanoparticles thus formed result from a simple physical encapsulation of the active principle.

Furthermore, Nederberg et al., *Biomacromolecules*, 2009, 10, 1460-1468, describe micelles comprising paclitaxel and a Y copolymer of polyethylene glycol and polylactic acid. However, here again, the micelles obtained result from the simple physical encapsulation of the paclitaxel with the said modified PEG-PLA copolymer.

However, this type of encapsulation exhibits the disadvantage of providing a poorly controlled degree of encapsulation, generally with a high risk of precipitation of the active principle. Furthermore, nanoencapsulation provides a release which is difficult to control and which depends on diffusion and biodegradation.

Another type of nanoparticles devoid of these disadvantages is therefore desirable. Thus, a covalent conjugation of the active principle and of the (co)polymer has been proposed.

This is because it is desirable to provide formulations with covalent encapsulation, making possible in particular a stoichiometric encapsulation, a limited precipitation of the active principle and/or a controlled release.

WO 99/17804 describes polymeric camptothecin derivatives resulting from the covalent conjugation of camptothecin and a methacryloyl-glycine-aminoacyl derivative.

However, this patent application relates only to camptothecin derivatives.

Covalent conjugates of polymers and taxoids have thus been provided. For example, Zhang et al., *Biomaterials*, 26(2005), 2121-2128 provide conjugates of paclitaxel with monomethoxy-polyethyleneglycol-polylactide (MPEG-PLA) via a diglycolic linker forming micelles in an aqueous medium. However, the active principle bonded to the end of the PLA is trapped in the hydrophobic region of the micelles thus formed and is in fact not very accessible.

Cheng et al., *Angew. Chem. Int. Ed.*, 2008, 47, 4830, have also described nanoparticles in which the active principle is grafted to the PLA end, in the not very accessible hydrophobic region.

It is thus desirable to improve the control of the release of the active principle from the (co)polymer in this type of formulation with covalent encapsulation which makes possible a stoichiometric encapsulation and a limited precipitation of the active principle.

The present invention proposes to respond to this technical problem by providing a covalent encapsulation referred to as conjugation by introducing a linker between the (co)polymer and the active principle and by significantly improving the accessibility of the active principle for hydrolysis.

Thus, the present inventors have discovered functionalized copolymers of polyethylene glycol and polylactic acid which meet the requirements set out above.

According to a first subject-matter, the present invention thus relates to conjugates of active principle and of a copolymer of polyethylene glycol and polylactic acid of formula (I):

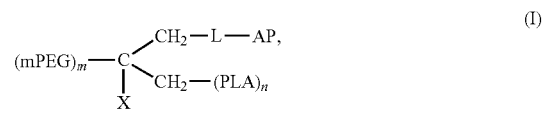

in the abovementioned formula (I):

mPEG is a methoxy-polyethylene glycol;

PLA is a polylactic acid;

m is the average molecular weight of the polyethylene glycol fragment (mPEG) and is comprised between 100 and 15 000 (expressed in Da), particularly 100-10000, more particularly between 1000 and 5000; such as approximately 2000;

n is the average molecular weight of the polylactic acid fragment and is an chosen between 1000 and 50 000 (expressed in Da), more particularly between 3000 and 20 000, still more particularly between 5000 and 20 000; such as approximately 10 000 or 14000;

AP is an active principle residue, preferably selected from taxoids,

L is a linker,

X is a hydrogen atom or an alkyl group optionally substituted by one or more substituents selected from halogen atoms or OR, CN, $CF_3$, NRR' or COOR groups, where R and R', which are identical to or different from one another, are a hydrogen atom or an alkyl group, and their pharmaceutically acceptable salts.

The term "average molecular weight" refers to the weight average molecular weight.

Generally, the AP residue is bonded to L by means of an OH group present in the AP.

Preferably, the PLA exhibits, at its optionally remaining free hydroxyl end, a protective group, for example a C(=O) alkyl group, such as a C(=O)$CH_3$ group. Preferably, X is a methyl group.

The $(mPEG)_m$ group may be represented by the formula:

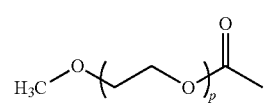

where p represents the average number of ethylene oxide units in the copolymer. Generally, p is comprised between 1 and 340, such as between approximately 20 and 110.

The (PLA)$_n$ group may be represented by the formula:

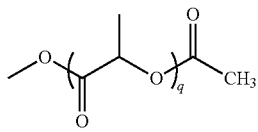

where q represents the average number of lactic acid units in the copolymer. Generally, q is comprised between 10 and 700, such as between approximately 40 and 300.

The conjugates according to the invention make possible a stoichiometric encapsulation of the active principle per chain of polymer comprised between 1 and 50%, generally up to 15% w/w, in particular around 5-6% and exhibit a low precipitation of the active principle in the aqueous phase and a controlled release of active principle by the linker. Furthermore, due to the specific Y structure of the mPEG/PLA copolymer, the active principle occurs at the hydrophobic/hydrophilic interface and is thus accessible to specific and nonspecific hydrolysis, making possible a controlled release in comparison with an active principle situated in the hydrophobic core.

In the above defined formula (I), AP may be selected from taxoids. The said taxoids are selected in particular from paclitaxel, docetaxel, cabazitaxel and larotaxel, such as of formulae:

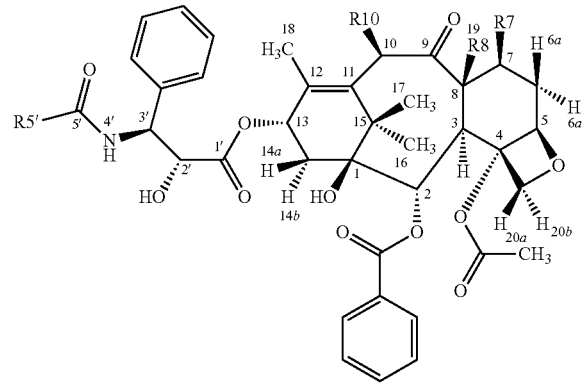

Paclitaxel : R10=—OC(=O)—CH$_3$, R5'=Ph, R7=OH; R8=CH$_3$

Docetaxel : R10=—OH; R5'=—O—C(CH$_3$)$_3$, R7=OH; R8=CH$_3$

Larotaxel: R10=—O—C(=O)—CH$_3$; R5'=—O—C(CH$_3$)$_3$; R7 and R8 form a cyclopropyl with the carbon atoms to which they are attached;

Cabazitaxel: R10=OCH$_3$; R7=—OCH$_3$; R8=CH$_3$; R5'=—O—C(CH$_3$)$_3$

Generally, in the case of the taxoids, the said OH group is present in the side chain of the taxoid in the 2' position, or in the 7 position.

More particularly, the said active principle is cabazitaxel, grafted in the 2' position.

In particular, the compounds of formula (I) are thus of formula:

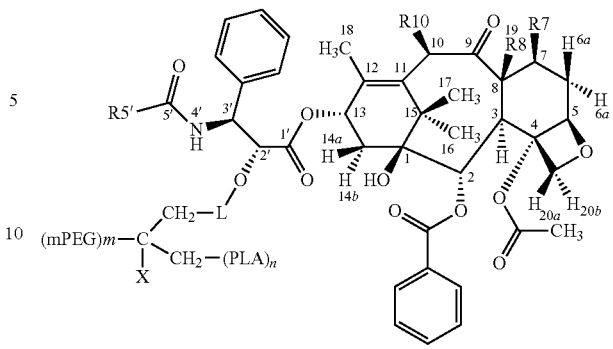

The term "linker" is understood to mean an alkyl chain comprising from 1 to 10 carbon atoms and exhibiting an oxygen atom at that of its ends connected to the mPEG/PLA copolymer and, at the other of its ends bonded to the AP, a group which reacts with a hydroxyl group present in the active principle, for example a carboxylic acid group. The alkyl chain can optionally be interrupted by one or more atoms or groups selected from —O—, —C(=O)—, —NR— or —O—C(=O)—NR—, —S—, —S—S—. The said linker can be selected in particular from dicarboxylate derivatives of succinic acid, glutaric acid or diglycolic acid. Mention may in particular be made of the dicarboxylate derivatives of succinic acid, glutaric acid and diglycolic acid, more preferably of the dicarboxylate derivative of succinic acid.

Preferably, the conjugates of formula (I) correspond to the formula (Ia):

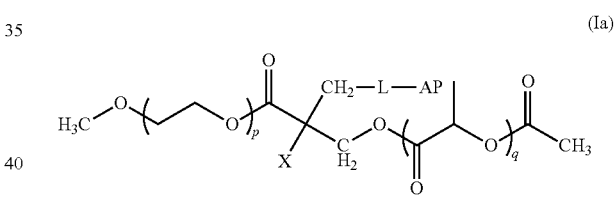

(Ia)

in which AP, X, L, p and q are defined as above.

More particularly, the compounds of formula (I) correspond to the following formula (Ib):

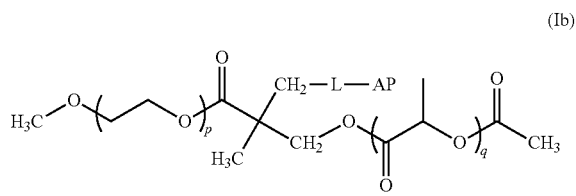

(Ib)

in which AP, L, p and q are defined as above.

According to a specific embodiment, the conjugates according to the present invention correspond to the above formula (Ib) in which L is a dicarboxylate derivative such as of succinic acid, glutaric acid or diglycolic acid.

The compounds of formula (I) can comprise one or more asymmetric carbon atoms. They can thus exist in the form of enantiomers or diastereoisomers. These enantiomers, diastereoisomers, and their mixtures, including racemic mixtures, are within the invention.

The compounds of formula (I) can exist in the form of bases or of addition salts with acids; this is in particular the case when X comprises the NRR' group. Such addition salts are within the invention.

These salts can be prepared with pharmaceutically acceptable acids but the salts of other acids, for example of use in the purification or the isolation of the compounds of formula (I), are also within the invention.

The compounds of formula (I) can also exist in the form of hydrates or solvates, namely in the form of combinations or associations with one or more molecules of water or with a solvent. Such hydrates and solvates are also within the invention.

In the context of the present invention:
- a halogen atom is understood to mean: a fluorine, a chlorine, a bromine or an iodine;
- an alkyl group is understood to mean: a saturated, linear or branched, (C1-C6) aliphatic hydrocarbon group. Mention may be made, by way of example, of the methyl, ethyl, propyl, isopropyl, butyl, isobutyl, tert-butyl or pentyl groups, and the like;
- aryl group is understood to mean: an aromatic cyclic group comprising between 5 and 10 carbon atoms. Mention may be made, as examples of aryl groups, of phenyl or naphthyl.

According to another subject-matter, the present invention relates to a process for the preparation of a conjugate according to the invention.

According to a first embodiment, the conjugate of formula (I) can be obtained by coupling the compound of formula (III):

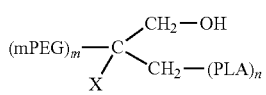
(III)

with a derivative of the said active principle corresponding to the formula:

AP-L-H where L is defined as in the general formula (I).

Thus, in the case of the taxoids, AP-L-H corresponds to the AP derivative in which the free OH group of the side chain of the taxoid has generally been esterified with the LH group via the carboxylic acid group of LH.

This coupling reaction can be carried out under esterification conditions known to a person skilled in the art, in particular in the presence of activating agents, such as carbodiimides (such as diisopropylcarbodiimide (DIPC)), with or without catalyst such as dimethylaminopyridine (DMAP). This reaction can be carried out in an appropriate solvent, such as dichloromethane, chloroform or ethyl acetate, at a temperature of between 0° C. and the reflux temperature of the solvent, more generally at ambient temperature.

The modified active principle AP-L-H can be obtained from the active principle AP by a coupling with the precursor of the desired linker L.

Thus, in the case where L represents a disuccinate compound, the precursor used is succinic anhydride. In the case where L represents a diglycolate group, the precursor used is diglycolic anhydride.

This coupling reaction is generally carried out in a solvent such as pyridine or in a chlorinated solvent in the presence of a catalyst, such as DMAP or pyridine, at a temperature of between 0° C. and the reflux temperature of the solvent under consideration, more generally at ambient temperature.

According to a second embodiment, the said process comprises the stage of coupling the said active principle AP exhibiting an OH group with a PEG/PLA copolymer of formula (II):

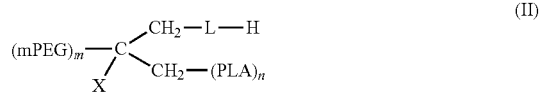
(II)

where LH exhibits an end carboxylic acid group COOH and mPEG, m, X, PLA and n are defined as in formula (I).

The said coupling reaction can be carried out under the normal esterification conditions in a solvent such as dichloromethane or chloroform, in the presence of activating agents, such as carbodiimides (such as diisopropylcarbodiimide (DIPC)), with or without catalyst, such as dimethylaminopyridine (DMAP). The reaction is generally carried out at a temperature between 0° C. and the reflux temperature of the solvent, more generally at ambient temperature.

The compound of formula (II) can be obtained from the compound of formula (III):

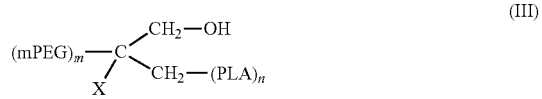
(III)

in which mPEG, m, PLA, n and X are defined as in the formula (I), by coupling with a precursor of the linker LH. Thus, in the case where LH represents the disuccinate group, the precursor used is succinic anhydride. When L is a diglycolate group, its precursor used is diglycolic anhydride. The precursors available according to the L group desired are generally known to the person skilled in the art and are commercially available.

The said coupling reaction generally takes place in a solvent, such as toluene or dichloromethane, in the presence of a catalyst, such as pyridine, at a temperature of between ambient temperature and the reflux temperature of the said solvent.

This reaction can be facilitated by using an appropriate catalyst, such as DMAP in particular.

The compound of formula (III) used according to one or other of the above synthetic routes is novel. Thus, the present invention also relates to a compound of formula (III):

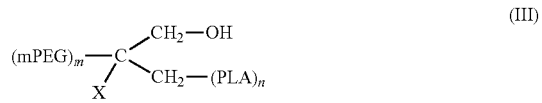
(III)

in which mPEG, PLA, m, n and X are defined as in the formulae (I), (Ia) and/or (Ib).

The compound (III) preferably corresponds to the following formulae (IIIa) and (IIIb):

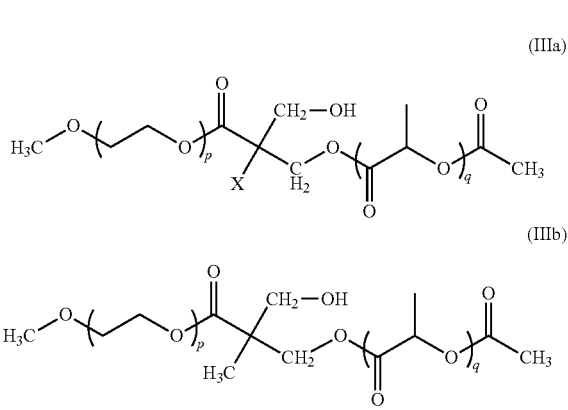

According to another subject-matter, the present invention also relates to the process for the preparation of the intermediate of formula (III). The said process comprises:

1. the stage of selective monoprotection of a hydroxyl group of the compound of formula (IV):

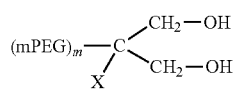

by means of an appropriate protective group, 2. the coupling of the monoprotected compound thus obtained with a precursor of the (PLA)$_n$ group, and 3. the deprotection of the protective group introduced during stage 1.

For stage 1, the appropriate protective group can be selected in particular from silyl derivatives, such as those described by T. W. Green and P. G. M. Wuts in *Protective Organic Groups in Organic Chemistry*, Wiley and Sons, 1991, or also J. F. W. McOmie in *Protective Groups in Organic Chemistry*, Plenum 13, 1973.

According to a particularly advantageous aspect, use is made, for the protection, of one or other of the following silyl derivatives:

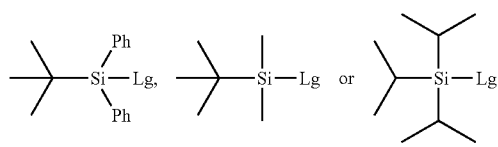

preferably

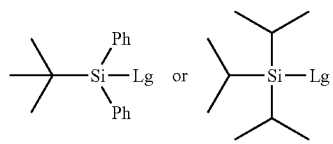

where Lg represents a leaving group, such as a halogen atom or a trifluoromethanesulphonate group, preferably a halogen atom, such as chlorine.

This reaction can be carried out under conditions known to a person skilled in the art, such as in the presence of a base, in particular an organic base, such as triethylamine, and of a solvent, such as dichloromethane, at a temperature of between ambient temperature and the reflux temperature of the solvent, in particular at approximately 40° C.

The stage 2) of coupling with a precursor of the (PLA)n can advantageously be carried out by ring opening polymerization (ROP) by means of the precursor 3,6-dimethyl-1,4-dioxane-2,5-dione. Purely by way of representation, this reaction can be illustrated by the following scheme:

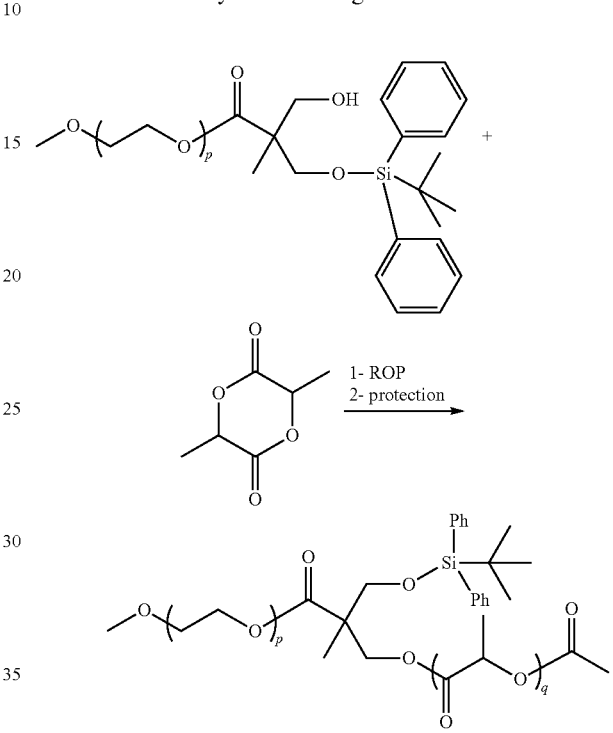

Generally, the ring opening polymerization is advantageously carried out in the presence of an organic catalyst, such as a thiourea (such as N-cyclohexyl-N'-[3,5-bis(trifluoromethyl)phenyl]thiourea), an amine (such as sparteine) and/or their mixtures, at a temperature between ambient temperature and the reflux temperature of the solvent. Mention may be made, as appropriate solvent, of dichloromethane.

The deprotection stage 3) can be carried out by application or adaptation of deprotection methods known to a person skilled in the art, such as those presented in the abovementioned Green et al. and McOmie et al. Use may advantageously be made of a fluoride, such as tetrabutylammonium fluoride (TBAF): Bu$_4$N$^+$,F$^-$, or trifluoroborane (BF$_3$.Et$_2$O). This reaction can be carried out in an appropriate solvent, such as THF or dichloromethane, at a temperature between ambient temperature and the reflux temperature of the reaction mixture, at approximately 40° C. for example, for a period of time sufficient to produce the desired degree of conversion.

The compound (IV):

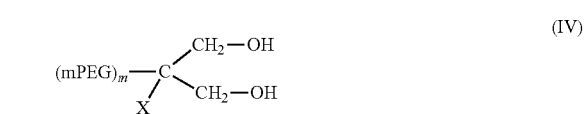

can be obtained from the compound of formula (V):

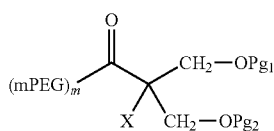

(V)

where mPEG, m and X are defined as above and Pg1 and Pg2, which are identical to or different from one another, either each independently represent a protective group for the hydroxyl group or Pg1 and Pg2 together form a protective group for the diol group by forming, together with the oxygen atoms to which they are attached, an acetal group which is optionally substituted, for example by a substituted or unsubstituted aryl group, by deprotection of the protective groups Pg1 and Pg2, in particular by catalytic hydrogenation Pd/C or acidic hydrolysis.

According to a specific aspect, Pg1 and Pg2 together form a benzylidene group, so that the product of formula (V) corresponds to the following formula (Va):

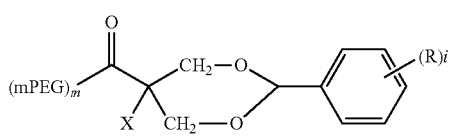

(Va)

where i is 0, 1 or 2 and each R identical or different independently represents H, or O(C1-C6)alkyl, preferably OMe.

The compound of formula (V) can be obtained by coupling the compound of formula (VI):

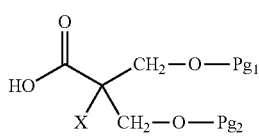

(VI)

and (mPEG)$_m$, in particular in the presence of coupling agents, such as 1,3-dicyclohexylcarbodiimide, 4-(dimethylamino)pyridinium p-toluenesulphonate (DPTS) and/or their mixtures, or DMAP. This reaction is generally carried out at ambient temperature.

The compound (VI) can be obtained by protection of the compound (VII):

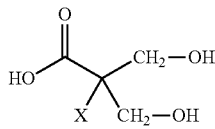

(VII)

according to the methods known to a person skilled in the art.

In the case in particular of the compound (VIa):

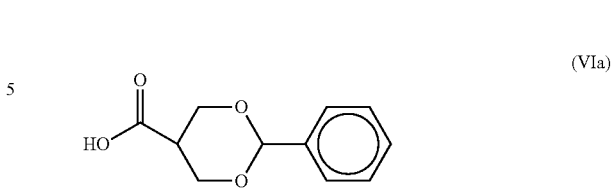

(VIa)

the latter can be obtained from the compound (VII) and benzaldehyde, in particular by application and/or adaptation of U. Annby et al., Tetrahedron Letters, 1998, 39, 3217.

The compound of formula (VII) is commercially available or can be obtained by application or adaptation of methods known to a person skilled in the art and/or within the scope of a person skilled in the art, in particular in view of the procedures described by Larock et al. in *Comprehensive Organic Transformations*, VCH Publishers, 1989.

The process according to the invention can additionally comprise the subsequent stage comprising the isolation and/or the purification of the desired compound. The desired compound thus prepared can be recovered from the reaction mixture by conventional means. For example, the compounds can be recovered by distilling the solvent from the reaction mixture or, if necessary, after distillation of the solvent from the mixture of the solution, by pouring the residue into water, followed by an extraction with a water-immiscible organic solvent, and by distilling the solvent from the extract. In addition, the compound can, if desired, be further purified by various techniques, such as recrystallization, reprecipitation or the various chromatography techniques, in particular size exclusion preparative chromatography.

According to another subject-matter, the present invention also relates to the nanoparticles comprising a conjuguate according to the invention. These nanoparticles generally exhibit a size of between 10 and 300 nm, generally between 20 and 200 nm.

Typically, they comprise a PLA core and a PEG corona, at the interface of which occurs the AP.

They can generally be prepared by nanoprecipitation, in particular by dissolution of the conjugate in an appropriate solvent, such as acetone, and evaporation of the said solvent.

According to another subject-matter, the present invention also relates to a pharmaceutical composition comprising a conjugate according to the invention.

According to another subject-matter, the present invention also relates to a conjugate according to the invention for use in the treatment and/or prevention of cancers.

FIGURES

EXAMPLES

Figure 1:
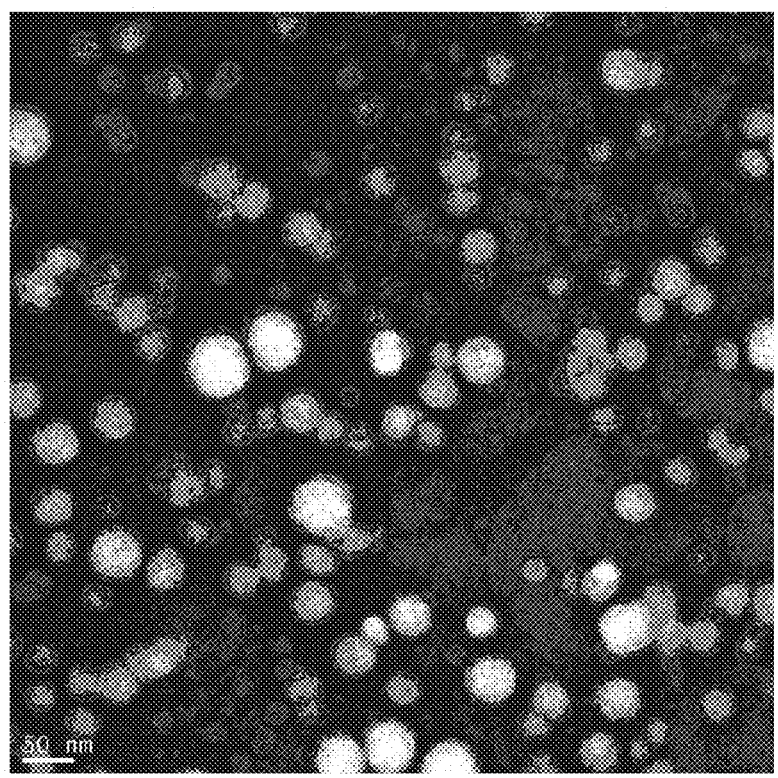
FIG. 1 represents the image obtained by transmission electron microscopy of the nanoparticles obtained according to the invention.

The following examples are given by way of representation and illustration of the present invention.

The solvents and reactants are used as is, except when this is specified. All the syntheses and polymerizations are carried out under an inert argon atmosphere using a standard Schlenk technique. The solvents are dried beforehand and are distilled before use: dichloromethane (DCM) over $CaH_2$, toluene over sodium or with a solvent purifier (Mbraun MB-SPS-800 system), tetrahydrofuran (THF) over sodium and diethyl ether over sodium. DL-lactide (PURAC) is purified by azeotropic distillation and recrystallization from toluene. It is subsequently sublimed and then stored under argon in a glove box.

Nuclear Magnetic Resonance (NMR): the NMR spectra are recorded at ambient temperature on Bruker Avance 300 MHz, Bruker Avance 400 MHz and Bruker Avance 500 MHz devices equipped with a cryoprobe. The chemical shifts δ in $^1H$ and $^{13}C$ are reported in ppm with respect to the residual solvent and the chemical shifts δ in $^{29}Si$ are reported in ppm with respect to $Me_4Si$ as external standard. The coupling constants J are given in hertz. The following abbreviations have been employed to describe the signals: s (singlet), br (broad), d (doublet), t (triplet), q (quartet) and m (multiplet).

Steric exclusion chromatography (SEC): the number-average molar masses $M_n$, the weight-average molar masses $M_w$ and the polydispersity indices ($M_w/M_n$) are measured by steric exclusion chromatography (SEC) at 35° C. with a triple detection line composed of an Alliance Waters e2695, of a MALS miniDAWN (Wyatt) light scattering detector, of a Viscostar-II (Wyatt) viscometer and of a Waters 2414 refractometer. THF is used as eluent at a flow rate of 1.0 ml/min. A Styragel (WAT054405) precolumn and two Shodex (KF-802.5 and KF-804) columns are used. The calibrations are carried out with polystyrene standards (400-100 000 g/mol). The samples are prepared in the following way: the product to be analyzed (10 to 20 mg) is dissolved in 1 ml of THF containing toluene as marker. The solution is subsequently filtered using a 0.45 μm filter.

Mass spectrometry: chemical ionization (DCI) mass spectra are recorded on a Thermo Fisher Scientific DSQ spectrometer.

Transmission electron microscopy (TEM): the morphology of the nanoparticles is observed by TEM using a JEOL-JEM 2100F microscope with an acceleration field of 200 keV. In order to prepare the samples, a few drops of the nanoparticulate dispersion, diluted ten fold (0.5 mg/ml), are incubated with 0.2% (w/v) of phosphotungstic acid for 30 min. The sample is subsequently placed on a copper grid and dried at ambient temperature.

Dynamic light scattering (DLS): the size (hydrodynamic diameter) of the nanoparticles is measured by DLS using a Zetasizer 3000 HS (Malvern).

The sample (5 mg/ml) is placed in a capillary cell after filtration (1.2 μm PVDF filter). The measurements are carried out at 25° C. with a detection angle of 90° C. The wavelength used is 633 nm.

In the examples below, indices m and n in $(mPEG)_m$ and $(PLA)_n$ are weight average molecular weight. n is experimentally determined from the weight obtained by the SEC analysis.

Synthesis of 5-methyl-2-phenyl-1,3-dioxane-5-carboxylic acid (Bn-Bis-MPA)(I)

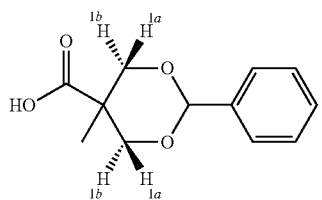

2,2'-bis(hydroxymethyl)propionic acid (Bis-MPA) (10 g, 74.6 mmol), benzaldehyde (8.3 g, 78.2 mmol) and methanesulphonic acid (MSA) (1.5 g, 15.6 mmol) are dissolved in 100 ml of toluene. The reaction medium is stirred at ambient temperature for 5 h. The solvent is subsequently evaporated under vacuum and then a 10% $NaHCO_3$ solution (300 ml) and ether (300 ml) are added until the residue has completely dissolved. The aqueous phase is recovered and a few drops of glacial acetic acid are added. After a strong evolution of gas, a white precipitate is formed. It is filtered off, rinsed with 20 ml of water and dried under vacuum overnight. $W_{obt}$=13.3 g, Y=80%.

$^1H$ NMR ($d_6$-acetone, 300 MHz): δ (ppm) 1.04 (s, 3H, —C—$CH_3$), 3.73 (d, 2H, 1a, $J^2_{Ha-Hb}$=11.4 Hz), 4.57 (d, 2H, 1b, $J^2_{Ha-Hb}$=11.3 Hz), 5.52 (s, 1H, $O_2$—CH—), 7.32 (m, 3H, ArH), 7.42 (m, 2H, ArH).

$^{13}C$ NMR ($d_6$-acetone, 75.5 MHz) : δ (ppm) 18.4 (—$CH_3$), 42.8 (Cq), 74.2 (—$CH_2$—), 102.1 (—$O_2$—CH—), 127.3 (aryl CH), 128.8 (aryl CH), 129.5 (aryl CH), 140.0 (aryl Cq), 176.2 (—COOH).

DCI calculated for $C_{12}H_{14}O_4$ [M+$NH_4$], 240.12; determined=239.90

Synthesis of methoxy-polyethylene glycol-benzylidene ($mPEG_{2000}$-$O_2Bn$) (II)

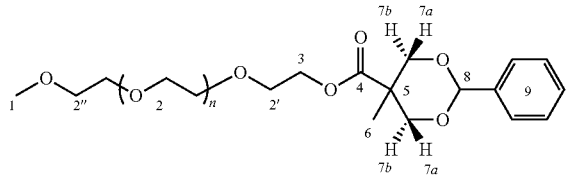

Methoxy-polyethylene glycol (average molecular weight: 2000 g/mol herein referred $mPEG_{2000}$) (10 g, 5 mmol) and the protected bis-MPA (I) (1.35 g, 6.1 mmol) are dissolved in 45 ml of anhydrous DCM in a 250 ml Schlenk vessel. 1-Ethyl-3-(3-dimethylaminopropyl)carbodiimide (EDCl) (0.96 g, 5 mmol) and 4-(dimethylamino)-pyridinium p-toluenesulphonate (DPTS) (0.6 g, 2 mmol) are subsequently added to the medium. The reaction medium is stirred at 40° C. under argon for 48 h. The reaction medium is subsequently extracted with 20 ml of a 1M HCl solution, 20 ml of a 10% $NaHCO_3$ solution and 20 ml of $H_2O$.

After drying the organic phase over $Na_2SO_4$, filtering and evaporating the solvent, the residue is precipitated from ether at 0° C. The precipitate is then filtered off and dried under vacuum overnight. A white solid is obtained. $W_{obt}$=9.68 g, Y=88%.

¹H NMR (CDCl₃, 300 MHz): δ 1.05 (s, 3H, 6), 3.37 (s, 3H, 1), 3.63 (bs, 180H, 2,2' & 7b), 4.36 (t, 2H, 3, J³$_{H-H}$=4.8 Hz), 4.66 (d, 2H, 7a, J²$_{Ha-Hb}$=11.5 Hz), 5.44 (s, 1H, 8), 7.32 (m, 3H, Ar/H), 7.42 (m, 2H, Ar/H).

¹³C NMR (CDCl₃, 75.5 MHz): δ (ppm) 17.8 (C6), 42.3 (C5), 58.9 (C1), 64.1 (C3), 68.9 (C7), 70.5 (C2), 71.8 (C2'), 73.4 (C2"), 101.2 (C8), 126.1 (aryl CH), 128.0 (aryl CH), 128.8 (aryl CH), 137.8 (aryl Cq), 173.8 (C4).

SEC: M$_n$=2867 g/mol, PI=1.06

Synthesis of methoxy-polyethylene glycol-diol (mPEG₂₀₀₀-(OH)₂) (III)

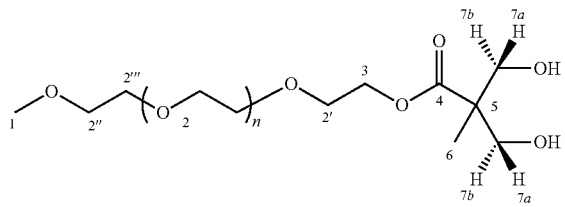

The compound (II) (9.5 g, 4.3 mmol) and palladium-on-charcoal (10% Pd/C) (0.95 g, 10% w/w) are mixed in a 250 ml two-necked round-bottomed Schlenk flask equipped with a balloon filled with hydrogen (H₂), followed by a vacuum-argon cycle. 40 ml of DCM and 40 ml of methanol (MeOH) are subsequently added. A vacuum-H₂ cycle is carried out. The reaction medium is stirred under static H₂ at At for 4 h. The mixture is subsequently filtered through Celite. The solvents are evaporated under vacuum and the residue is dried under vacuum overnight. A yellowish solid is obtained. W$_{obt}$=8.7 g, Y=95%.

¹H NMR (CDCl₃, 300 MHz): δ 1.11 (s, 3H, 6), 3.37 (s, 3H, 1), 3.63 (bs, 180H,), 3.69-3.78 (m, 4H, 7a & 7b), 4.33 (t, 2H, 3, J³$_{H-H}$=4.8 Hz).

¹³C NMR (CDCl₃, 125.7 MHz): δ 16.9 (C6), 49.5 (C5), 58.8 (C1), 63.2 (C3), 67.1 (C7), 68.7 (C2'), 70.4 (C2), 71.8 (C2"), 72.6 (C2'"), 175.5 (C4).

Synthesis of mPEG₂₀₀₀-(OH)—Y—(OTBDPS) (IV)

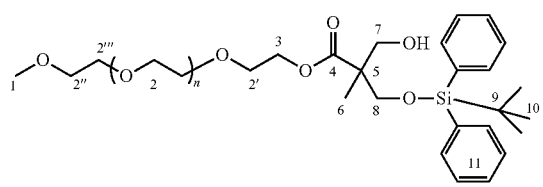

The compound (III) (4 g, 1.90 mmol) is dissolved in 18 ml of anhydrous DCM in a 100 ml Schlenk vessel. Triethylamine (TEA), distilled over KOH (0.4 g, 3.95 mmol) is subsequently added and then tert-butyldiphenylchlorosilane (TBDPSiCl) (1.1 g, 3.92 mmol) is added dropwise at 0° C. The reaction medium is stirred at 40° C. and under argon. After 24 h, the salt formed is filtered off and then the organic phase is extracted with a 1M HCl solution (15 ml), then an NaHCO₃ solution (15 ml) and, finally, H₂O (15 ml). The organic phase is dried over Na₂SO₄. After filtration, the mixture is concentrated under vacuum and then the residue is precipitated from ether at 0° C. The white precipitate obtained is then filtered off, washed and dried under vacuum. The product is subsequently dried using an azeotrope in toluene. The product is stored in a glove box. W$_{obt}$=4.1 g, Y=90%.

RMN ¹H (CDCl₃, 300 MHz): δ 1.02 (s, 9H, 10), 1.19 (s, 3H, 6), 3.37 (s, 3H, 1), 3.63 (br, 180H, 2/2'/2"/2'"), 3.73-3.80 (m, 4H, 7 & 8), 4.26 (t, 2H, 3, J³$_{H-H}$=4.8 Hz), 7.35-7.64 (m, 10H, 11).

RMN ¹³C (CDCl₃, 75.5 MHz): δ 16.9 (C6), 19.1 (C9), 26.5 (010), 50.3 (C5), 58.7 (C1), 63.1 (C3), 65.6 (C7), 66.4 (C8), 68.6 (C2'), 70.3 (C2), 71.7 (C2'"), 72.3 (C2"), 127.5 (CH aryle), 129.5 (CH aryle), 132.9 (Cq aryle), 135.3 (CH aryle), 174.8 (C4).

RMN ²⁹Si (CDCl₃, 59.6 MHz): δ −4.33 (—O—Si—).

Synthesis of an mPEG₂₀₀₀-PLA₁₄₀₀₀-Y—OTBDPS copolymer (V)

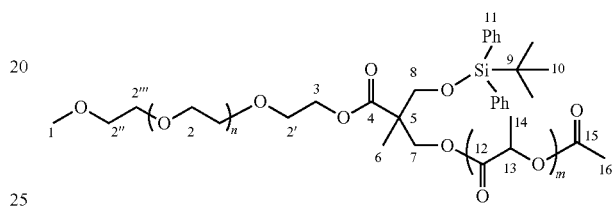

The macroinitiator (IV) (0.8 g, 0.34 mmol) and DL-lactide (5 g, 35 mmol, DP 100) are dissolved in 25 ml of anhydrous DCM. A solution of catalyst (10 ml, 4 equivalents of thiourea (N-cyclohexyl-N'-[3,5-bis(trifluoromethyl)phenyl]thiourea) and 4 equivalents of (−)-sparteine are subsequently added. The reaction medium is stirred at 35° C. under argon until the lactide has been completely consumed, which action is monitored by ¹H NMR. After 6 h, acetic anhydride (166 μl, 1.71 mmol) and 4-dimethylaminopyridine (DMAP) (4.5 mg, 0.35 mmol) are added to the reaction medium. The latter is stirred for an additional 1 h. The mixture is subsequently concentrated under vacuum and then precipitated from 150 ml of MeOH at 0° C. The white precipitate formed is filtered off, washed with 20 ml of MeOH and then dried under vacuum overnight.

RMN ¹H (CDCl₃, 500 MHz): δ 1.02 (s, 9H, 10), 1.19 (s, 3H, 6), 1.58 (br, 595H, 14), 2.12 (s, 3H, PLA: 16), 3.37 (s, 3H, 1), 3.63 (br, 180H, 2/2'/2"/2'"), 3.73-3.80 (m, 2H, 8), 4.20-4.40 (m, 4H, 3 & 7), 5.16 (br, 192H, 13), 7.35-7.64 (m, 10H, 11).

RMN ¹³C (CDCl₃, 125.7 MHz): δ 16.6 (C14 & C6), 20.4 (C9), 26.6 (C10), 48.5 (C5), 58.8 (C1), 63.5 (C3), 65.0 (C7), 66.6 (C8), 68.9 (C13), 68.2 (C2'), 70.1 (C2), 71.7 (C2'"), 72.2 (C2"), 127.7, 129.8, 132.8, 135.5 (C11), 169.50 (C12 & C15), 174.82 (C4).

Average molecular weight (by NMR): M=16150 g/mol

The ring opening polymerization (ROP) reaction was also similarly carried out with a 35 and 150 equivalents of the lactide leading to mPEG₂₀₀₀-PLA₅₀₀₀ and mPEG₂₀₀₀-PLA₂₁₀₀₀ copolymers Synthesis of an mPEG₂₀₀₀-PLA₁₄₀₀₀-Y—OH copolymer (VI)

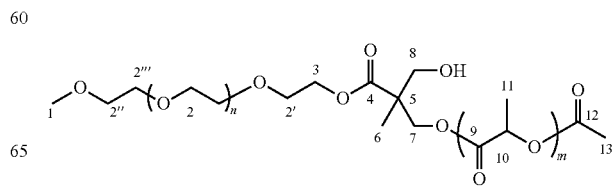

The copolymer (V) (3.96 g, 0.28 mmol) is dissolved in 40 ml of anhydrous THF. A 1M solution of tetrabutylammonium fluoride (TBAF) in THF (1.5 ml, 1.5 mmol) is subsequently added dropwise. The reaction medium is stirred at 30° C. under argon for 7 h. The THF is subsequently evaporated under vacuum. The residue is dissolved in 15 ml of DCM and subsequently precipitated from 800 ml of ether at 0° C. The white precipitate is filtered off and then dried under vacuum overnight. $W_{obt}$=2.14 g, Y=55%.

RMN $^1$H (CDCl$_3$, 300 MHz): δ 1.57 (br, 590H, PLA : 11), 2.12 (s, 3H, PLA : 13), 3.37 (s, 3H, 1), 3.63 (br, 180H, 8, 2/2'/2''/2'''), 4.33 (m, 4H, 3 & 7), 5.15 (br, 186H, PLA : 10).

RMN $^{13}$C (CDCl$_3$, 75.5 MHz): δ 16.5 (PLA : C11), 48.5 (C5), 58.7 C1), 63.4 (C3), 64.2 (C7), 66.5 (C8), 68.8 (PLA : 010), 68.2 (C2'), 70.1 (C2), 71.7 (C2'''), 72.2 (C2''), 169.5 (PLA : C9), 174.8 (PEG : C4).

Average molecular weight (by NMR): M=15495 g/mol

Protection was also carried out with triisopropylchlorosilane (TIPSCl) as followed.

In a schlenk of 25 ml, the mPEG-Diol derivative (0.5 g, 0.24 mmol) is dissolved in 5 ml of anhydrous DCM. Triéthylamine (TEA) (distilled on KOH) (0.2 g, 2.01 mmol) is then added, and Tris-isopropyl chlorosilane (TIPSCl) (0.40 g, 2 mmol) is added dropwise at 0° C. The reaction mixture is stirred at 40° C. and under argon. After 24 hours, the formed salt is filtered and the organic phase is extracted with a HCl 1M solution (5 ml), and a NaHCO$_3$ solution (5 ml) and H$_2$O (5 ml). The organic phase is dried on Na$_2$SO$_4$. Following filtration, the mixture is concentrated under vacuum and the residue is precipitated in ether at 0° C. The white precipitate is then filtered, washed and dried under vacuum. The product is then dried with an azeotrope in toluene. The product is stored in a hermetic box. $M_{obt}$=0.4 g, R=74%.

NMR $^1$H (CDCl$_3$, 500 MHz): δ 0.98-1.03 (br, 21H), 1.16 (s, 3H), 3.37 (s, 3H), 3.63 (m, 180H), 3.73-3.80 (m, 4H), 4.26 (t, 2H, $J^3_{H-H}$=4.8 Hz).

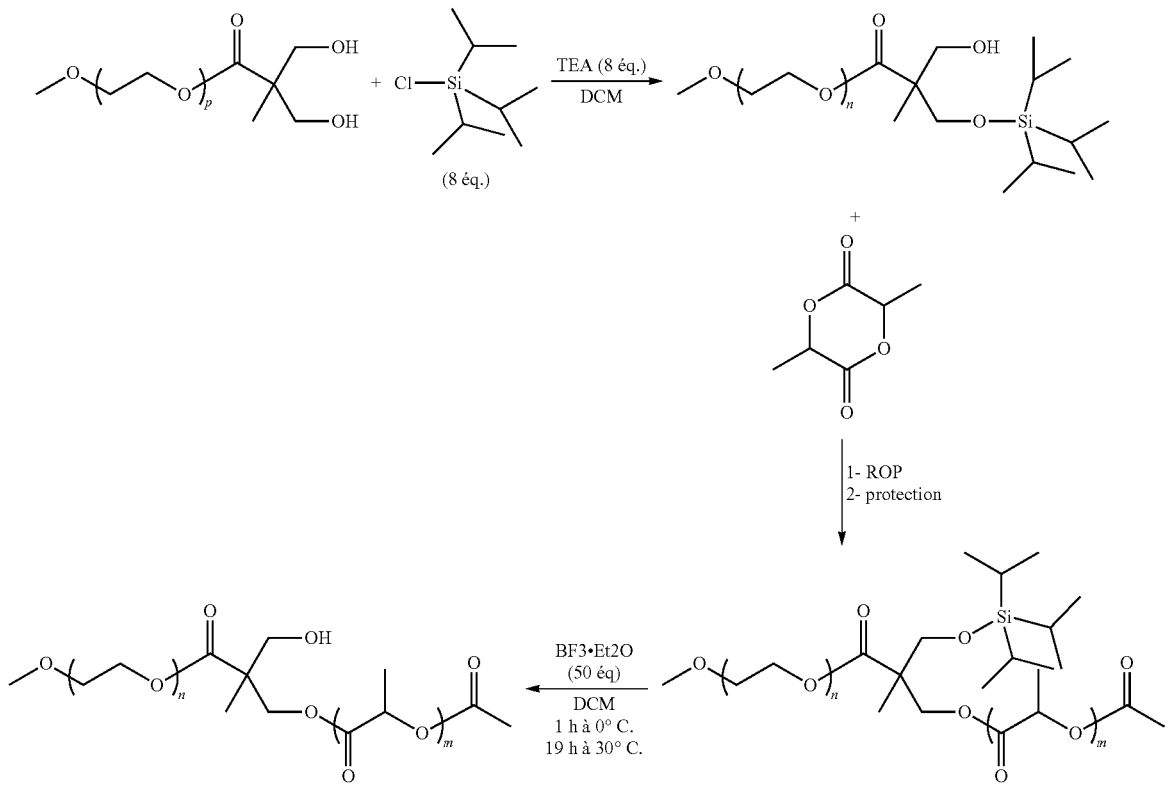

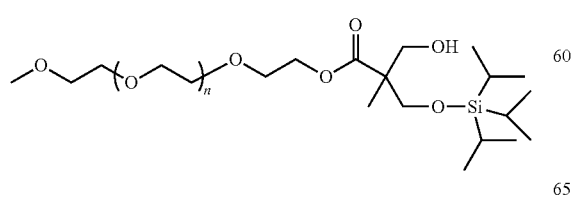

Synthesis of mPEG$_{2000}$-(OH)—Y—(OTIPS)

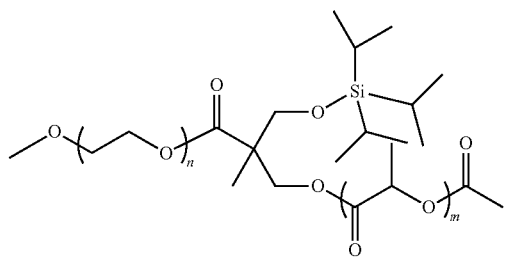

Synthesis of a copolymer mPEG$_{2000}$-PLA$_{10000}$-Y—OTIPS (V')

The macroinitiator (0.18 g, 79.6 μmol) and the DL-Lactide (0.8 g, 5.6 mmol, 70 equivalents) are dissolved in 7 ml of anhydrous DCM. A solution of the catalyst (1 ml, 4 equivalents of thiuorea (N,N'-cyclohexyl-3,5-bis[trifluoromethyl] phenyl thiourea) and 2 equivalents of (+)-spartéine) are then added. The reaction mixture is stirred at 35° C. under argon until full consumption of the lactide, as controlled by ¹HNMR. After 3 hours, the acetic anhydride (39 μl, 0.40 mmol) and the 4-Dimethylaminopyridine (DMAP) (10 mg, 82 μmol) are added to the reaction mixture. This is stirred for one more hour. The mixture is then concentrated under vacuum, then precipitated in 50 ml ether at 0° C. The white precipitate is then filtered, washed with 20 ml of MeOH, then dried under vacuum for one night.

$M_{obt}$=1 g, R~75%

NMR ¹H (CDCl₃, 500 MHz): δ 0.98-1.03 (br, 21H), 1.16 (s, 3H), 1.58 (m, 423H), 2.12 (s, 3H), 3.37 (s, 3H, 1), 3.63 (m, 180H), 3.73-3.80 (m, 2H), 4.20-4.40 (m, 4H), 5.16 (m, 141H, 13).

SEC: $M_w$=13628 g/mol, $M_n$=11850 g/mol, IP=1.15

Synthesis of a copolymer mPEG$_{2000}$-PLA$_{10000}$-Y—OH (VI')

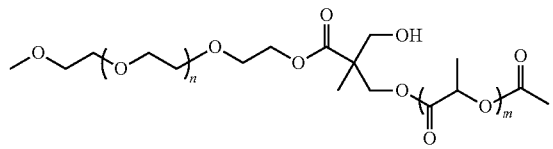

The protected copolymer (1 g, 71 μmol) is dissolved in 10 ml of anhydrous DCM. BF₃.Et₂O (0.5 g, 3.56 mmol) is then added, dropwise, at 0° C. The reaction mixture is stirred at 0° C. under argon for one hour and then at 30° C. for 19 hours. Then, DCM is evaporated under vacuum. The residue is solubilized in 5 ml of DCM, and then precipitated in 50 ml of ether at 0° C., washed with 20 ml of MeOH and then with 20 ml of pentane. The white precipitate is filtered and dried under vacuum for one night.

$M_{obt}$=0.85 g, R~85%.

NMR ¹H (CDCl₃, 500 MHz): δ 1.58 (m, 425H), 2.12 (s, 3H), 3.37 (s, 3H), 3.63 (m, 180H), 4.33 (m, 4H), 5.16 (m, 142H).

SEC: $M_w$=13925 g/mol, $M_n$=11800 g/mol, IP=1.18

Synthesis of cabazitaxel-2'-Succinyl (VII)

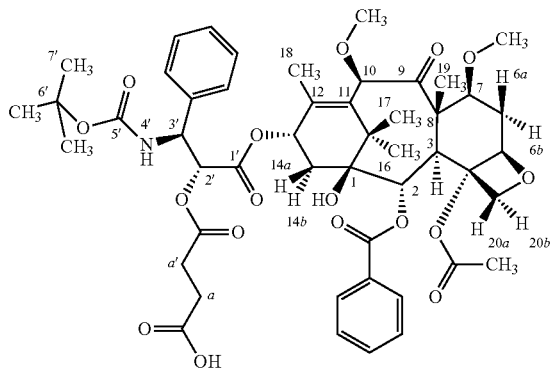

Cabazitaxel (0.2 g, 0.24 mmol) is dissolved in 4 ml of pyridine distilled over KOH. Succinic anhydride (0.2 g, 2 mmol) is subsequently added. The reaction medium is stirred at 30° C. under argon. The reaction is monitored by thin layer chromatography (TLC) (DCM/MeOH: 9/1). After 8 h, the pyridine is evaporated under vacuum and the residue is purified with a chromatographic column (eluent: CHCl₃/MeOH: gradient from 99/1 down to 97/3). The various fractions are subsequently evaporated in order to obtain a white powder dried under vacuum. $W_{obt}$=0.180 g, Y=80%.

RMN ¹H (CDCl₃, 300 MHz): δ 1.19 (s, 3H, 16), 1.20 (s, 3H, 17), 1.35 (s, 9H, 7'), 1.63 (s, 1H, —OH tertiary), 1.70 (s, 3H, 19), 1.78 (m, 1H, 6a), 1.86 (s, 3H, 18), 2.15 (s, 6H, —CH₃acetone), 2.18-2.33 (m, 2H, 14a & 14b), 2.34 (s, 3H, —CH₃ acetyl in 4), 2.65 (m, 5H, —CH₂ succinic a, a' & 6b), 3.28 (s, 3H, —OCH₃ en 7), 3.44 (s, 3H, —OCH₃ en 10), 3.80 (d, 1H, 3, J=7.5 Hz), 3.84 (dd, 1H, 7, J=6.5 & 10.5 Hz), 4.16 (d, 1H, 20a, J=8.5 Hz), 4.28 (d, 1H, 20b, J=8.5 Hz), 4.80 (s, 1H, 10), 4.95 (d, 1H, 5, J=10 Hz), 5.28-5.44 (br, 2H, 2'/4'), 5.61 (d, 1H, 2, J=7.5 Hz), 6.19 (b, 1H, 13), 7.31, 7.38, 7.47, 7.59, (m, 9H, ArH), 8.10 (d, 2H, H ortho benzoate).

RMN ¹³C (CDCl₃, 75.5 MHz): δ 10.8 (C19), 15.1 (C18), 21.2 (C16), 23.2 (CH₃ acétyle), 27.3 (C17), 28.35, 28.62 (—CH₂ succinic a & a') 28.7 (C7'), 32.6 (C6), 35.7 (C14), 43.8 (C15), 47.9 (C3), 56.7 (C3'), 57.4 (C8), 57.5 (OCH₃ en C7), 57.8 (OCH₃ en C10), 73.1 (C13), 74.7 (C2'), 75.0 (C2), 77.0 (C20), 79.2 (C1), 80.7 (C6'), 81.2 (C7), 82.3 (C4), 83.1 (C10), 84.6 (C5), 127.3-138.9 (Ar), 136.2 (C11), 139.1 (C12), 155.8 (C5'), 167.5 (CO benzoate), 168.7 (CO acetyl in 4), 170.0-174.0 (C1', —COO— succinic), 205.4 (C9).

Synthesis of the mPEG$_{2000}$-PLA$_{14000}$-Y-succinyl-2'-cabazitaxel Conjugate (VIII)

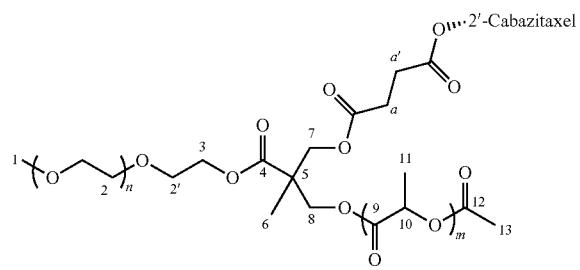

The copolymer (VI) (2 g, 163 μmol) and cabazitaxel-2'-succinyl (VII) (0.33 g, 353 μmol) are dissolved in 40 ml of anhydrous DCM. N,N'-Diisopropylcarbodiimide (DIPC) (45 mg, 357 μmol) and then DMAP (45 mg, 368 μmol) are subsequently added. The reaction medium is stirred at 35° C. under argon for 24 h. The organic phase is subsequently extracted using a 1M HCl solution (30 ml), a 10% NaHCO₃ solution (30 ml) and water (30 ml). The organic phase is subsequently dried over Na₂SO₄ and then filtered. It is concentrated under vacuum and then the residue is precipitated in 400 ml of MeOH. After filtration, the precipitate is dried under vacuum overnight. $W_{obt}$=1.5 g, Y=75%.

¹H NMR (CDCl₃, 500 MHz): after precipitation of the crude product from MeOH, quantification of complete coupling (100%). The same chemical shifts of the compounds (VI) and (VII) are detected, with a ratio 1/1.

¹³C NMR: Shift of the signals of the succinic linker —(CH₂)—: 28.13 and 26.71 ppm, in addition to the chemical shifts of the compounds (VI) and (VII).

Average molecular weight(by NMR) : M=16430 g/mol

Nanoparticles Formulation:

The conjugate (VIII) (20 mg) obtained above is dissolved in 2 ml of acetone (10 mg/ml). The solution obtained is added dropwise to 4 ml of deionized water, under stirring. The acetone is evaporated, for example on a rotary evaporator. A final concentration of conjugate of 5 mg/ml is thus obtained.

The nanoparticles thus obtained were characterized as follows:

TEM: A photograph obtained is represented in FIG. 1. A mean diameter of 27 nm is observed.

Figure 2:
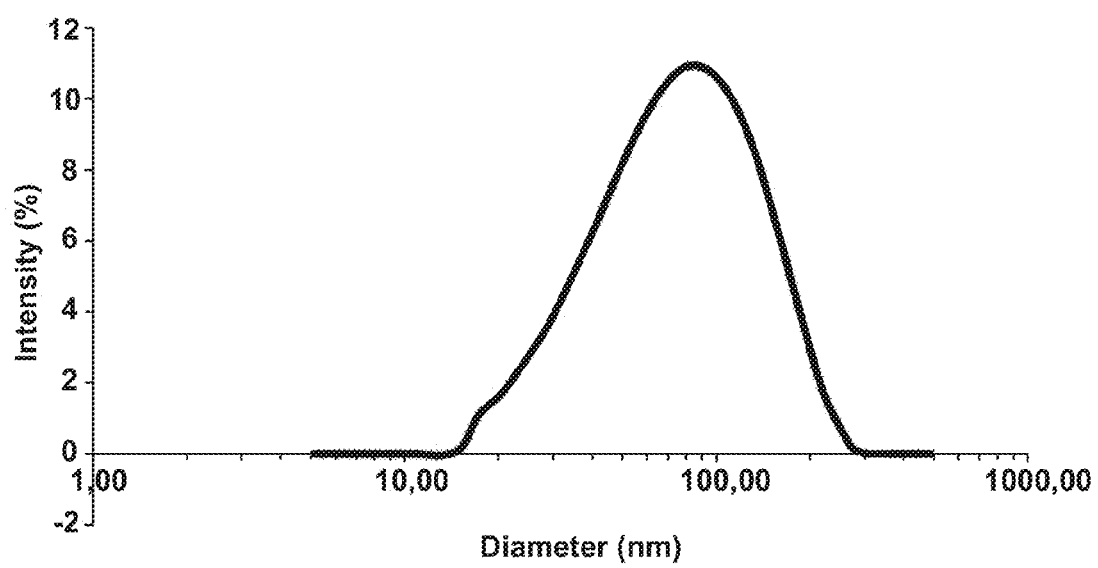
FIG. 2 represents the distribution in sizes of the nanoparticles by DLS (Dynamic Light Scattering) measurement at T 0 and at T+3 weeks.

DLS: The sample is filtered (1,2 μm): A mean diameter of 62 nm is obtained. The distribution remained unchanged for 3 weeks. Results are illustrated in FIG. 2.

Synthesis of the mPEG$_{2000}$-PLA$_{10000}$-Y-succinyl-2'-cabazitaxel Conjugate (VIII')

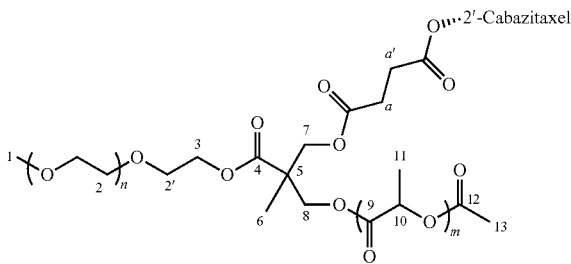

14 g of copolymer (VI') (Mw 12700 g /mol) and 2.24 g of succinyl-cabazitaxel are dissolved in dry dichloromethane and 7 g of activated molecular sieves 4A as powder are added. The solution is stirred for 10 minutes at RT and 310 mg DMAP and 305 mg DIPC are added. The solution is stirred at 35° C. for 24 h. After filtration, the solution is concentrated to dryness at 40° C. under vaccum. The residue is stirred with 2.8 litrers methanol and 1 ml dichloromethane for 2 hours at 0° C. The suspension is filtered and the solid is washed with 100 ml methanol. After drying at RT overnight, 14 g of a white power is obtained. 7.5 g of the solid is repurified in 749 ml methanol by stirring overnight at RT to obtain after filtration and drying 7.1 g of a white powder.

$^1$H NMR Spectrum (600 MHz, d in ppm, CDCl$_3$-d$_1$): 1.21 (m, 9 H); 1,36 (s, 9 H); 1.42 to 1.72 (m, 468 H); 1.79 (m, 1 H); 1.98 (broad s, 3 H); 2.13 (s, 3 H); 2.18 (m, 1 H); 2.29 (m, 1 H); 2.43 (broad s, 3 H); 2.54 to 2.77 (m, 5 H); 3.31 (s, 3 H); 3,38 (s, 3 H); 3.44 (s, 3 H); 3.50 to 3.78 (m, 180 H); 3.84 (d, J=6.5 Hz, 1 H); 3.89 (dd, J=6.5 & 10.6 Hz, 1 H); 4.08 to 4.41 (m, 8 H); 4,82 (s, 1 H); 4.99 (d, J=9.8 Hz, 1 H); 5.01 to 5.31 (m, 156 H); 5.32 (m, 1 H); 5.47 (m, 2 H); 5.64 (d, J=6.5 Hz, 1 H); 6.24 (broad t, J=9.0 Hz, 1 H); 7.31 (m, 3 H); 7.40 (t, J=7.9 Hz, 2 H); 7.50 (t, J=7.9 Hz, 2 H); 7.61 (t, J=7.9 Hz, 1 H); 8.11 (d, J=7.7 Hz, 2 H)

SEC M$_w$=13530 g/mol, M$_n$=11770 g/mol, IP=1.15

Nanoparticles Formulation:

1) 30 mg of PLA-PEG-Y-succinyl-cabazitaxel (VIII') is dissolved in 1.5 mL of acetone. The solution is added dropwise into 3 mL of WFI, under stirring (500 rpm during 20 minutes). Acetone is then evaporated at 37° C. under vacuum using Rotavapor (from 300 to 45 mbar during 30 minutes).

The final volume of nanodispersion is then adjusted to 3 mL, to compensate for any loss of water during evaporation.

Final concentration of the nanodispersion: 10 mg/mL

Mean diameter (using DLS)=43 nm, PDI=0.14

2) 1 g of PLA-PEG-Y-succinyl cabazitaxel (VIII') was dissolved in 50 mL of acetone at room temperature, under agitation. The organic solution was filtered through a 0.45 μm Nylon filter, and then introduced in a 50 mL Hamilton syringe. 0.2 g of Solutol HS15 (Macrogol 15 Hydroxystearate) and 0.04 g of sodium deoxycholate were dissolved in 450 mL of WFI with stirring. This aqueous solution was filtered on a 0.22 μm filter. The organic solution was poured, at a rate of 20 mL/h, in the aqueous phase, by using a syringe pump. In order to allow a homogeneous dispersion, a teflon tube, connected to the syringe, dived into the aqueous phase. Nanoparticles of size ≤100 nm were then obtained by nanodispersion (average size of 30 nm, PDI=0.14), measured using Malvern Nanosizer (Quasi Elastic Light Scattering).

The acetone and some of the water were eliminated by using a rotary evaporator, under vacuum, at 37° C. The final nanodispersion concentration was between 10 and 200 mg/g. The size of the nanoparticles stayed ≤100 nm (average size of 30 nm, for all concentrations). Bigger particles could be withdrawn by filtration on 0.45 μm.

Synthesis of mPEG-PLA-succinyl-larotaxel (IX)

Preparation of Succinyl-Larotaxel

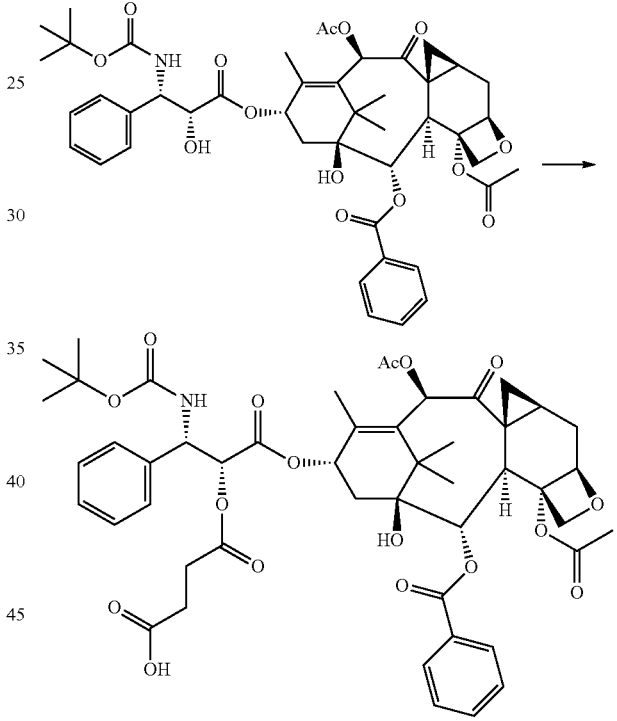

In a flask are added under nitrogen, 2.36 g (2.72 mmol) of larotaxel dihydrate, 47 ml dichloromethane, 2.72 g (27.19 mmol) succinic anhydride and 33 mg (0.27 mmol) DMAP. The solution is heated to 30° C. overnight then washed twice with 47 ml water. After drying of the organic solution with MgSO4, the solution is concentrated to dryness at 40° C. under reduced pressure. The dry extract is treated with 3 volumes of diisopropyl ether and the suspension is stirred for 2 hours, filtrated and the solid washed twice with 2 volumes of diisopropyl ether. After drying at 40° C. under reduced pressure, 2.28 g of a white powder are obtained.

NMR $^1$H Spectrum (500 MHz, δ in ppm, CDCl$_3$-d): 1.26 (s, 3 H); 1.28 (s, 3 H); 1.32 (s, 9 H); 1.38 (m, 1 H); 1.68 (m, 1 H); 1.93 (s, 3 H); 2.11 (d, J=15.9 Hz, 1 H); 2,19 (Broad s, 4 H); 2.25 (dd, J=4.8 & 10.3 Hz, 1 H); 2.35 (m, 1 H); 2.38 (s, 3 H); 2.49 (td, J=4.8 & 15.9 Hz, 1 H); 2.61 to 2.82 (m, 4 H); 4.07 (d, J=8.6 Hz, 1 H); 4.12 (d, J=7.5 Hz, 1 H); 4.31 (d, J=8.6 Hz, 1

H); 4.75 (Broad d, J=4.8 Hz, 1 H); 5.35 to 5.51 (m, 2 H); 5.69 (d, J=7.5 Hz, 1 H); 6.23 (Broad t, J=9.4 Hz, 1 H); 6.34 (s, 1 H); 7.30 (m, 3 H); 7.39 (t, J=7.8 Hz, 2 H); 7.51 (t, J=7.8 Hz, 2 H); 7.60 (t, J=7.8 Hz, 1 H); 8.16 (d, J=7.8 Hz, 2 H)

Conjugation of succinyl-larotaxel with copolymer (VI')

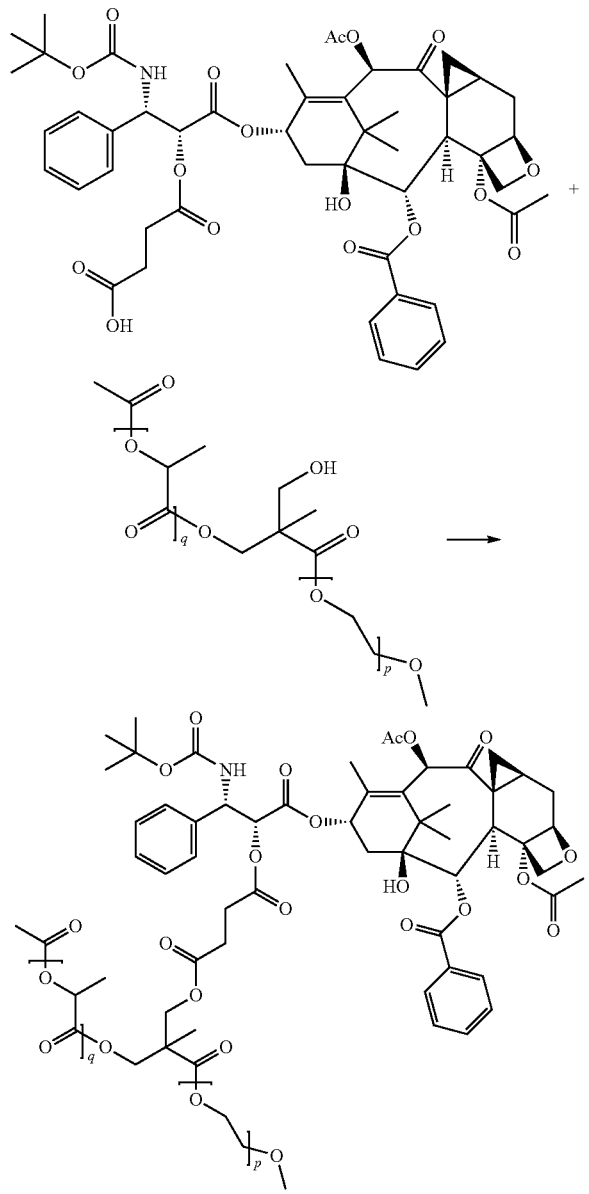

In a 25 ml flask are added under nitrogen 0.2 g of mPEG-PLA-Y-OH copolymer (VI') (0.0157 mmol), 31.6 mg (2.2 eq) of succinyl-larotaxel in 4 ml de DCM then 100 mg of activated molecular sieves 4A in powder. After 10 min stirring, is added 4.4 mg (2.3 eq.) DMAP and 4.3 mg (2.2 eq.) DIPC. The suspension is stirred for 24 h at 35° C. then filtrated (0.22 microns). The organic phase is concentrated to dryness et the extract is treated with 40 ml methanol and 2 drops dichloromethane. The suspension is stirred for 2 h at RT, then filtrated and the solid is dried at RT under reduced pressure to obtain 174 mg of the expected compound.

NMR $^1$H Spectrum (500 MHz, δ in ppm, CDCl$_3$-d): 1.22 (m, 3 H); 1.24 (s, 3 H); 1.27 (s, 3 H); 1.29 (s, 9 H); 1.35 to 1.85 (m, 512 H); 1.91 (Broad s, 3 H); 2.08 to 2.75 (m, 9 H); 2.13 (s, 3 H); 2.20 (s, 3 H); 2.41 (Broad s, 3 H); 3.39 (s, 3 H); 3.48 to 3.81 (m, 192 H); 4.02 to 4.39 (m, 8 H); 4.75 (Broad d, J=4.0 Hz, 1 H); 5.01 to 5.33 (m, 169 H); 5.34 (m, 1 H); 5.40 to 5.52 (m, 2 H); 5.68 (d, J=7.6 Hz, 1 H); 6.26 (Broad t, J=9.0 Hz, 1 H); 6.34 (s, 1 H); 7.30 (m, 3 H); 7.39 (t, J=7.7 Hz, 2 H); 7.51 (t, J=7.7 Hz, 2 H); 7.61 (t, J=7.7 Hz, 1 H); 8.18 (d, J=7.7 Hz, 2 H)

SEC $M_w$=14140 g/mol $M_n$=11260 g/mol, D=1.25

Nanoparticles Formulation:

30 mg of PLA-PEG-Y-succinyl-larotaxel is dissolved in 1.5 mL of acetone. The solution is added drop-wise into 3 mL of water for injection (WFI), under stirring (500 rpm during 20 minutes). Acetone is then evaporated at 37° C. under vacuum using Rotavapor.

The final volume of nanodispersion is then adjusted to 3 mL, to compensate for any loss of water during evaporation Final concentration of the nanodispersion: 10 mg/mL Mean diameter (using DLS)=48 nm, PDI=0.17

Synthesis of mPEG-PLA-glutaryl-cabazitaxel (X)

Preparation of Glutaryl-cabazitaxel

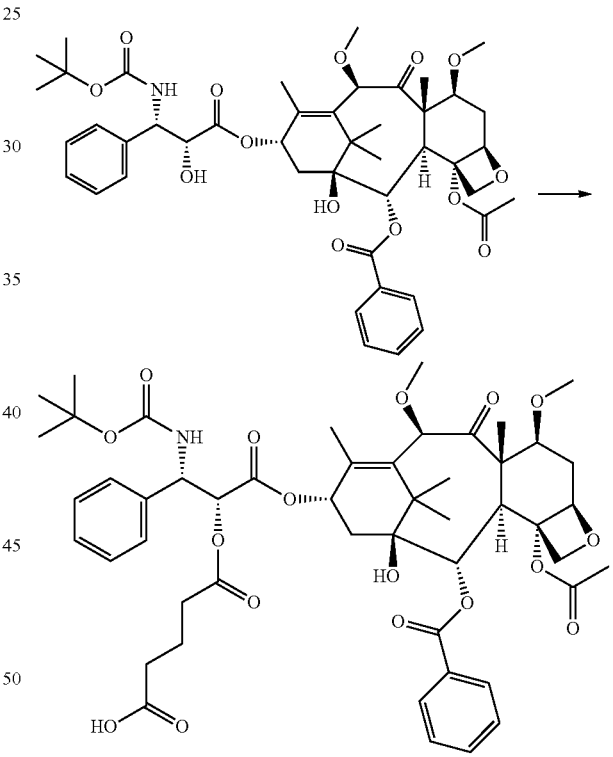

In a 500 ml flask are added under nitrogen, 10 g (11.24 mmol) of cabazitaxel acetone solvate, 200 ml dichloromethane, 13.51 g (112.45 mmol) glutaric anhydride and 0.14 g (1.12 mmol) DMAP. The solution is heated to 30° C. overnight then washed several times with 100 ml water. After drying of the organic solution with MgSO4, the solution is concentrated to dryness at 40° C. under reduced pressure. The dry extract is treated with 10 volumes of diisopropyl ether and the suspension is filtrated and the solid washed twice with 2 volumes of diisopropyl ether. After drying at RT under reduced pressure, 6.75 g of a white powder is obtained.

NMR $^1$H Spectrum (500 MHz, δ in ppm, CDCl$_3$-d): 0.97 (s, 3 H); 0.98 (s, 3 H); 1.38 (s, 9 H); 1.50 (m, 5 H); 1.79 (m, 6

H); 2.24 (s, 3 H); 2.28 (t, J=7.3 Hz, 2 H); 2.46 (t, J=7.4 Hz, 2 H); 2,66 (m, 1 H); 3.21 (s, 3 H); 3.29 (s, 3 H); 3.59 (d, J=7.1 Hz, 1 H); 3.75 (dd, J=6.6 et 10.7 Hz, 1 H); 4.02 (s, 2 H); 4.47 (s, 1 H); 4.70 (s, 1 H); 4.95 (broad d, J=10.7 Hz, 1 H); 5.02 to 5.12 (m, 2 H); 5.37 (d, J=7.1 Hz, 1 H); 5.81 (broad t, J=9.0 Hz, 1 H); 7.18 (t, J=7.7 Hz, 1 H); 7.36 (d, J=7.7 Hz, 2 H); 7.43 (t, J=7,7 Hz, 2 H); 7.66 (t, J=7.7 Hz, 2 H); 7.74 (t, J=7.7 Hz, 1 H); 7.85 (d large, J=9.1 Hz, 1 H); 7.98 (d, J=7.7 Hz, 2 H); 12.13 (very broad s, 1 H).

Conjugation of glutaryl-cabazitaxel with copolymer (VI')

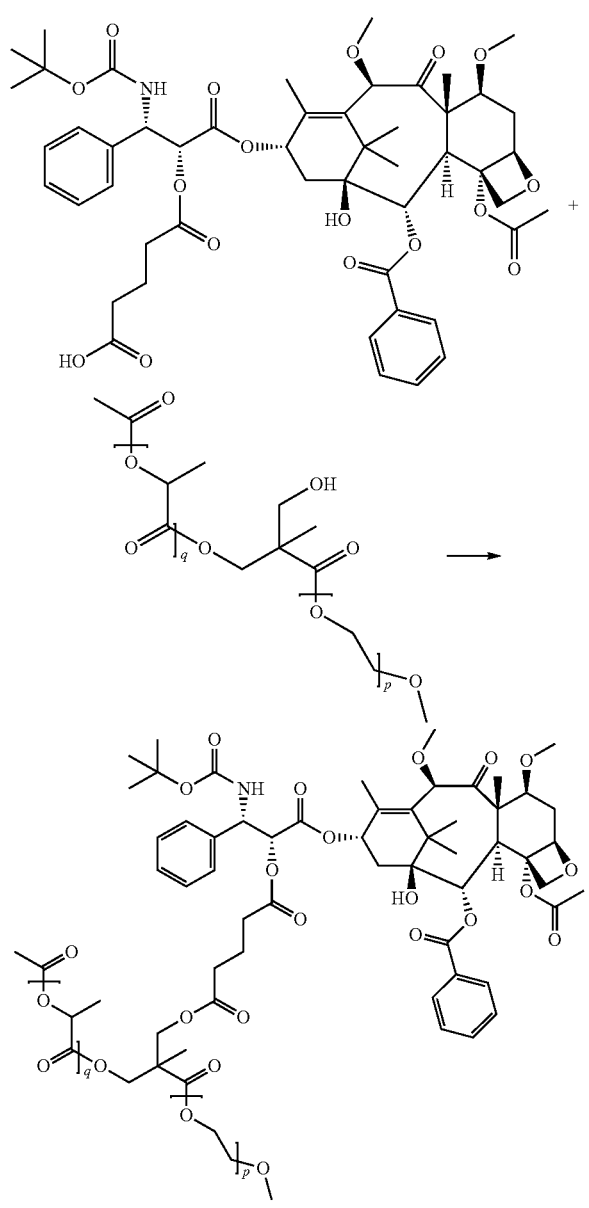

In a 25 ml flask are added under nitrogen 0.2g of mPEG-PLA-Y—OH copolymer (VI') (0.0157 mmol), 31.6 mg (2.2 eq) of glutaryl-cabazitaxel in 4 ml de DCM then 100 mg of activated molecular sieves 4A in powder. After 10 min stirring, is added 4.4 mg (2.3 eq.) DMAP and 4.3 mg (2.2 eq.) DIPC. The suspension is stirred for 24 h at 35° C. then filtrated (0.22 microns). The organic phase is concentrated to dryness et the extract is treated with 40 ml methanol and 2 drops dichloromethane. The suspension is stirred for 2 h at RT, then filtrated and the solid is dried at RT under reduced pressure to obtain 170 mg of the expected compound.

NMR $^1$H Spectrum (500 MHz, δ in ppm, CDCl$_3$-d): 1.21 (s, 3 H); 1.22 (s, 3 H); 1.25 (m, 3 H); 1.35 (s, 9 H); 1.40 to 1.70 (m, 452 H); 1.72 (s, 3 H); 1.80 (m, 1 H); 1.87 (m, 2 H); 2.00 (s, 3 H); 2.13 (s, 3 H); 2.15 to 2.51 (m, 6 H); 2.45 (Broad s, 3 H); 2.71 (m, 1 H); 3.32 (s, 3 H); 3.39 (s, 3 H); 3.45 (s, 3 H); 3.48 to 3.81 (m, 172 H); 3.86 (d, J=7.3 Hz, 1 H); 3.91 (dd, J=6.3 & 11.0 Hz, 1 H); 4.10 to 4.40 (m, 8 H); 4.83 (s, 1 H); 5.00 (d, J=10.7 Hz, 1 H); 5.01 to 5.33 (m, 152 H); 5.35 (m, 1 H); 5.44 to 5.63 (m, 2 H); 5.66 (d, J=7.3 Hz, 1 H); 6.27 (Broad t, J=9.0 Hz, 1 H); 7.32 (m, 3 H); 7.40 (t, J=7.7 Hz, 2 H); 7.50 (t, J=7.7 Hz, 2 H); 7.61 (t, J=7.7 Hz, 1 H); 8.12 (d, J=7.7 Hz, 2H)

SEC M$_w$=14140 g/mol M$_n$=11210 g/mol, D=1.26

Nanoparticles Formulation:

30 mg of PLA-PEG-Y-glutaryl-cabazitaxel is dissolved in 1.5 mL of acetone. The solution is added drop-wise into 3 mL of WFI, under stirring (500 rpm during 20 minutes). Acetone is then evaporated at 37° C. under vacuum using Rotavapor.

The final volume of nanodispersion is then adjusted to 3 mL, to compensate for any loss of water during evaporation.

Final concentration of the nanodispersion: 10 mg/mL

Mean diameter (using DLS)=60 nm, PDI=0.21

Synthesis of mPEG-PLA-diglycolyl-cabazitaxel (XI)

Preparation of diglycolyl-cabazitaxel

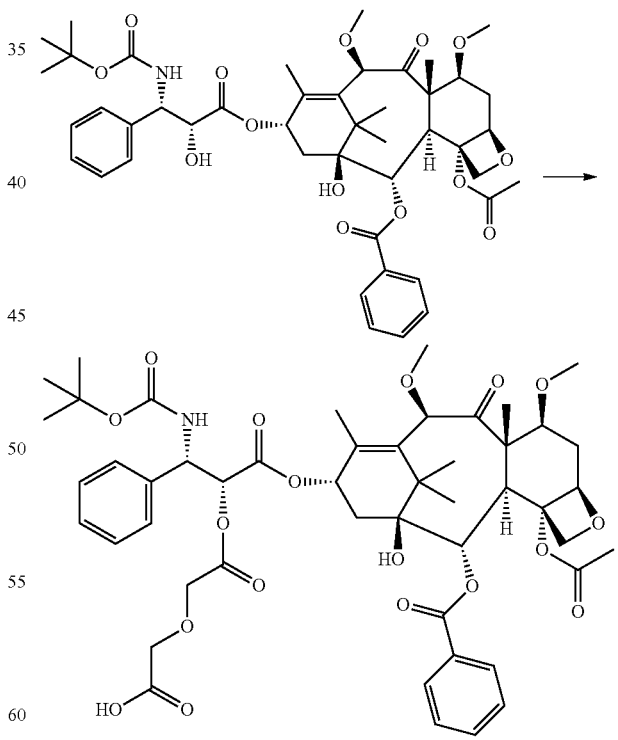

In a 250 ml flask are added under nitrogen, 5 g (5.62 mmol) of cabazitaxel acetone solvate, 100 ml dichloromethane, 6.53 g (56.22 mmol) diglycolic anhydride and 0.107 (0.56 mmol) DMAP. The solution is heated to 22° C. overnight then washed twice with 50 ml water. After drying of the organic solution with MgSO4, the solution is concentrated to dryness at 40° C. under reduced pressure. The dry extract is treated with 4 volumes of diisopropyl ether and the suspension is stirred for 30 minutes then filtrated and the solid washed twice with 2 volumes of diisopropyl ether. After drying at 40° C. under reduced pressure, 5.04 g of a white powder is obtained.

$^1$H NMR Spectrum (500 MHz, δ in ppm, CDCl$_3$-d): 0.96 (s, 3 H); 0.98 (s, 3 H); 1,37 (m, 9 H); 1,44 to 1,58 (m, 2 H); 1,51 (s, 3 H); 1,80 (Broad s, 4 H); 2,23 (s, 3 H); 2.67 (m, 1 H); 3.21 (s, 3 H); 3.28 (s, 3 H); 3.58 (d, J=7.3 Hz, 1 H); 3.75 (dd, J=6.8 & 10.5 Hz, 1 H); 4.02 (s, 2 H); 4.13 (s, 2 H); 4.31 (d, J=17.0 Hz, 1 H); 4.38 (d, J=17.0 Hz, 1 H); 4.51 (s, 1 H); 4.70 (s, 1 H); 4.95 (d, J=10.5 Hz, 1 H); 5.06 (m, 1 H); 5.16 (d, J=8.5 Hz, 1 H); 5,37 (d, J=7,3 Hz, 1 H); 5,82 (Broad t, J=9,4 Hz, 1 H); 7,19 (t, J=7,8 Hz, 1 H); 7.36 (d, J=7.8 Hz, 2 H); 7.43 (t, J=7.8 Hz, 2 H); 7.66 (t, J=7.8 Hz, 2 H); 7.73 (t, J=7.8 Hz, 1 H); 7.88 (d, J=9.3 Hz, 1 H); 7.97 (d, J=7.8 Hz, 2 H); 12.78 (very broad s, 1H)

Conjugation of diglycolyl-cabazitaxel with copolymer (VI')

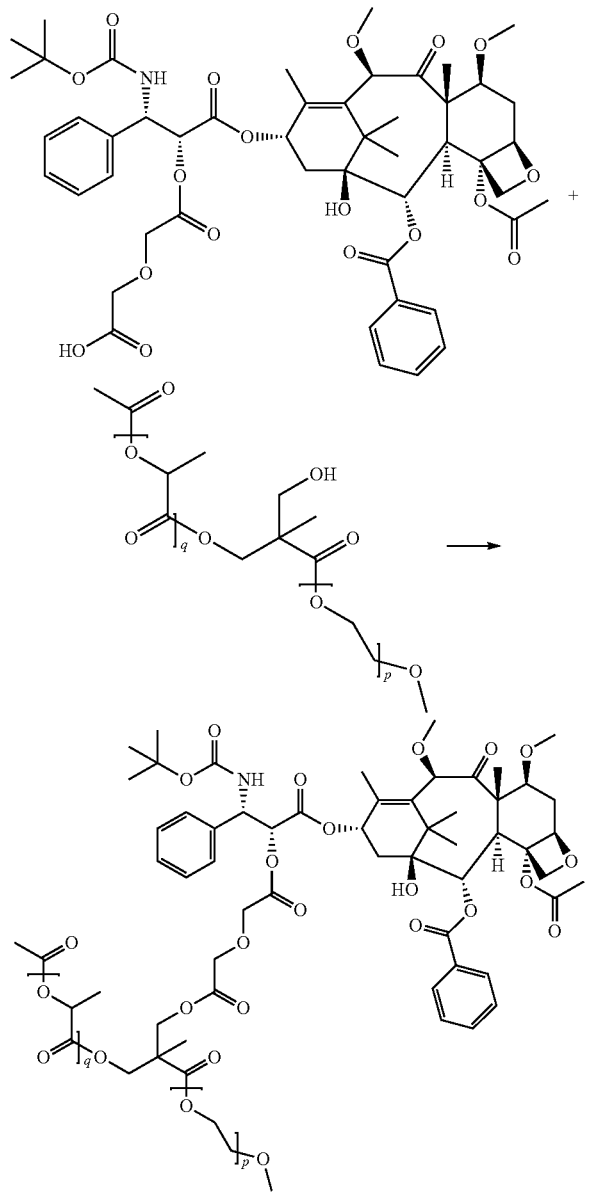

In a 25 ml flask are added under nitrogen 0.2 g of mPEG-PLA-Y—OH copolymer (VI') (0.0157 mmol), 32.3 mg (2.2 eq) of diglycolyl-cabazitaxel in 4 ml de DCM then 100 mg of activated molecular sieves 4A in powder. After 10 min stirring, is added 4.4 mg (2.3 eq.) DMAP and 4.3 mg (2.2 eq.) DIPC. The suspension is stirred for 24 h at 35° C. then filtrated (0.22 microns). The organic phase is concentrated to dryness and the extract is treated with 40 ml methanol and 2 drops dichloromethane. The suspension is stirred for 2 h at RT, then filtrated and the solid is dried at RT under reduced pressure to obtain 184 mg of the expected compound.

NMR $^1$H Spectrum (500 MHz, δ in ppm, CDCl$_3$-d): 1.21 (s, 3 H); 1.22 (s, 3 H); 1.26 (m, 3 H); 1.35 (s, 9 H); 1.40 to 1.70 (m, 486 H); 1.72 (s, 3 H); 1.80 (m, 1 H); 2.01 (Broad s, 3 H); 2.13 (s, 3 H); 2.21 (m, 1 H); 2.32 (m, 1 H); 2.45 (Broad s, 3 H); 2.71 (m, 1 H); 3.31 (s, 3 H); 3.38 (s, 3 H); 3.45 (s, 3 H); 3.48 to 3.81 (m, 180 H); 3.86 (d, J=7.3 Hz, 1 H); 3.91 (dd, J=6.6 & 11.0 Hz, 1 H); 4.08 to 4.40 (m, 8 H); 4.83 (s, 1 H); 5.02 (d, J=10.7 Hz, 1 H); 5.03 to 5.33 (m, 162 H); 5.40 to 5.57 (m, 3 H); 5.67 (d, J=7.3 Hz, 1 H); 6.29 (Broad t, J=9.0 Hz, 1 H); 7.31 (m, 3 H); 7.40 (t, J=7.7 Hz, 2 H); 7.50 (t, J=7.7 Hz, 2 H); 7.60 (t, J=7.7 Hz, 1 H); 8.11 (d, J=7.7 Hz, 2H)

SEC $M_w$=14830 g/mol, $M_n$=11920 g/mol, D=1.24

Nanoparticles Formulation:

30 mg of PLA-PEG-Y-diglycolyl-cabazitaxel is dissolved in 1.5 mL of acetone. The solution is added drop-wise into 3 mL of WFI, under stirring (500 rpm during 20 minutes). Acetone is then evaporated at 37° C. under vacuum using Rotavapor (from 300 to 45 mbar during 30 minutes).

The final volume of nanodispersion is then adjusted to 3 mL, to compensate for any loss of water during evaporation.

Final concentration of the nanodispersion: 10 mg/mL

Mean diameter (using DLS)=52 nm, PDI=0.18

In vitro release studies of Cabazitaxel Conjugates Nanoparticles Formulations

The in vitro release kinetics of free Cabazitaxel from the three Cabazitaxel conjugates nanoparticle formulations, i.e. PLA-PEG-Y-succinyl-cabazitaxel, PEG-Y-glutaryl-cabazitaxel, and PLA-PEG-Y-diglycolyl-cabazitaxel has been assessed in plasma (buffered previously with a 500 mM phosphate buffer to a final concentration of 10 mM in plasma) obtained from Sprague Dawley rat, using a high performance liquid chromatography (HPLC) technique. To the vials containing plasma aliquots, standard cabazitaxel or cabazitaxel conjugates nanoparticle formulations (1 mg/mL) have been added using a micropipette to achieve a final volume of 8004. The vials are then placed at 37° C. on an agitator (agitation speed 250 rpm). The sample analysis was carried out at 0 h, 1 h, 2 h, 4 h, 16 h and 24 h.

At every time interval, 100 μL of sample was collected into a vial containing 0.3 mL of acetonitrile:water 85:15 v/v, and agitated for 5 min to allow the precipitation of proteins and the extraction of free cabazitaxel. The contents were then subjected to centrifugation at 10,000 rpm for 10 min, and the clear supernatant was collected and subjected for quantification using HPLC.

The HPLC conditions employed were as follows:

Column: 150 mm Zorbax SB phenyl 3.5 μm

Flux: 1 mL min ; column temperature was 30° C.

Ultraviolet (UV) dual detection mode at 230 nm (principal used for titration) and 210 nm Isocratic mobile phase: Acetonitrile 60%/water 40%/Trifluoroacetic acid 0.006%

Retention time for Cabazitaxel=4.1 min

Results are summarized in the table below:

TABLE

In vitro data of cabazitaxel conjugates nanoparticle formulations (i.e. PLA-PEG-Y-succinyl-cabazitaxel, PLA-PEG-Y-glutaryl-cabazitaxel, and PLA-PEG-Y-diclycolyl-cabazitaxel) in rat plasma

| Time (h) | PLA-PEG-Y-succ-cbz NPs | PLA-PEG-Y-glutaryl-cbz NPs | PLA-PEG-Y-diglycolyl-cbz NPs |
|---|---|---|---|
| 0 | 0 | 0 | 2.20 |
| 1 | 0.84 | 1.31 | 5.36 |
| 2 | 1.68 | 2.30 | 8.67 |
| 4 | 3.30 | 5.29 | 14.81 |
| 18 | 17.35 | 23.51 | 49.39 |
| 24 | 20.16 | 31.72 | 55.09 |

Figure 3:
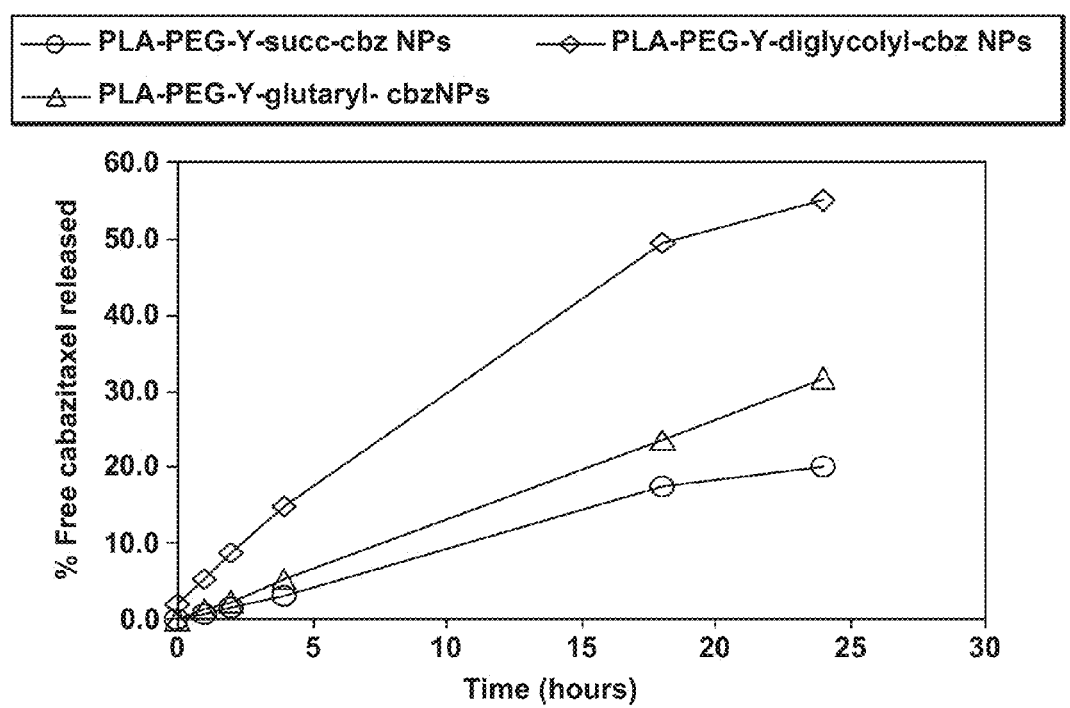
FIG. 3 represents the in vitro profiling of cabazitaxel conjugates nanoparticle formulations (i.e. PLA-PEG-Y-succinyl-cabazitaxel, PLA-PEG-Y-glutaryl-cabazitaxel, and PLA-PEG-Y-diclycolyl-cabazitaxel) in rat plasma.

The in vitro release studies in rat plasma have revealed that all the cabazitaxel conjugates formulations showed sustained drug release profile, and the conjugates synthesized using different linkers have resulted in different release profiles (FIG. 3). The conjugate containing succinyl linker has showed the slowest release profile (~17% free cabazitaxel released in 24 h), followed by the conjugate containing glutaryl linker (~27% free cabazitaxel released in 24 h), whereas a relatively rapid release was observed in the case of the conjugate containing diglycolyl linker (~47% free Cabazitaxel released in 24 h). Particularly, in the case of PLA-PEG-Y-succinyl-cabazitaxel, the release of succinyl-cabazitaxel has been quantified using HPLC. The results revealed the release of a negligible concentration of succinyl-cabazitaxel (<1% of cabazitaxel present initially in the nanoparticles) from the formulation. Overall, the order of the drug release was as follows: PLA-PEG-Y-diglycolyl-cabazitaxel>PLA-PEG-Y-glutaryl-cabazitaxel>PLA-PEG-Y-succinyl-cabazitaxel nanoparticles. These results indicate that the cabazitaxel conjugates with different linkers allow different in vitro release profiles.

The inventions claimed is:

1. Conjugate of an active principle and of a copolymer of polyethylene glycol and polylactic acid of formula (I):

$$(mPEG)_m - \underset{X}{\overset{CH_2-L-AP}{C}} - CH_2-(PLA)_n, \quad (I)$$

in which:
mPEG is a methoxy-polyethylene glycol;
PLA is a polylactic acid;
m is the average molecular weight of the polyethylene glycol fragment (mPEG) and is comprised between 100 and 15 000 (expressed in Da);
n is the average molecular weight of the polylactic acid fragment and is comprised between 1000 and 50 000 (expressed in Da);
AP is an active principle residue;
L is a linker, such that L is a dicarboxylate derivative of succinic acid, glutaric acid or diglycolic acid,
X is a hydrogen atom or an alkyl group optionally substituted by one or more substituents selected from halogen atoms, OR, CN, $CF_3$, NRR' and COOR groups, where R and R', which are identical to or different from one another, are a hydrogen atom or an alkyl group,
and their pharmaceutically acceptable salts.

2. Conjugate according to claim 1, such that the AP residue is bonded to L by means of an OH group present in the AP.

3. Conjugate according to claim 1, such that the said AP is a taxoid.

4. Conjugate according to claim 3, such that the said taxoid is selected from paclitaxel, docetaxel, cabazitaxel and larotaxel.

5. Conjugate according to claim 1, such that the said active principle is cabazitaxel, grafted in the 2' position.

6. Conjugate according to claim 1, such that the said PLA exhibits, at its optionally remaining free hydroxyl end, a protective group.

7. Conjugate according to claim 1, corresponding to the formula (Ia):

$$H_3C-O-(CH_2CH_2O)_p-CO-C(X)(CH_2-L-AP)(CH_2-O-(CO-CH(CH_3)-O)_q-CO-CH_3) \quad (Ia)$$

in which L, AP, and X are as defined according to claim 1 and p is comprised between 1 and 340, and q is comprised between 10 and 700.

8. Conjugate according to claim 1, corresponding to the following formula (Ib):

$$H_3C-O-(CH_2CH_2O)_p-CO-C(CH_3)(CH_2-L-AP)(CH_2-O-(CO-CH(CH_3)-O)_q-CO-CH_3) \quad (Ib)$$

in which L, and AP are as defined according to claim 1 and and p is comprised between 1 and 340, and q is comprised between 10 and 700.

9. Process for the preparation of a conjugate according to claim 1, comprising the coupling of a compound of formula (III):

$$(mPEG)_m - \underset{X}{\overset{CH_2-OH}{C}} - CH_2-(PLA)_n \quad (III)$$

with a derivative of the said active principle corresponding to the formula:

AP-L-H where mPEG, m, PLA, n, X, AP and L are defined according to claim 1.

10. Compound of formula (III):

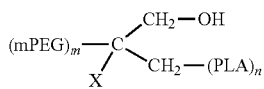
(III)

in which mPEG, PLA, m, n and X are defined according to claim 1.

11. Process for the preparation of the compound of formula (III) according to claim 10 comprising:
1. the stage of selective monoprotection of a hydroxyl group of the compound of formula (IV):

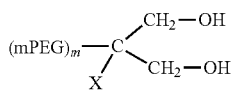
(IV)

by means of an appropriate protective group,
2. the coupling of the monoprotected compound thus obtained with a precursor of the (PLA)$_n$ group, and
3. the deprotection of the protective group introduced in stage 1,
in which mPEG is a methoxy-polyethylene glycol;
m is the average molecular weight of the polyethylene glycol fragment (mPEG) and is comprised between 100 and 15 000 (expressed in Da);
PLA is a polylactic acid;
n is the average molecular weight of the polylactic acid fragment and is comprised between 1000 and 50 000 (expressed in Da);
and X is a hydrogen atom or an alkyl group optionally substituted by one or more substituents selected from halogen atoms, OR, CN, CF$_3$, NRR' and COOR groups, where R and R', which are identical to or different from one another, are a hydrogen atom or an alkyl group.

12. Process according to claim 11, such that the monoprotection is carried out by means of

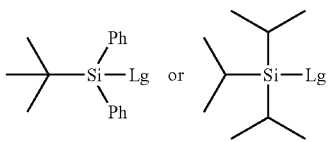

where Lg represents a leaving group, such as a halogen atom or a trifluoromethanesulphonate group.

13. Process according to claim 11 such that stage 2 is carried out by ring opening polymerization (ROP) by means of the precursor 3,6-dimethyl-[1,4]-dioxane-2,5-dione.

14. Nanoparticles comprising a conjugate according to claim 1.

15. Pharmaceutical composition comprising a conjugate according to claim 1.

16. A method for the treatment and/or prevention of cancers in a patient in need thereof comprising administering to said patient a therapeutically effective amount of the conjugate of claim 1.

* * * * *